United States Patent [19]

Ottow et al.

[11] Patent Number: 5,843,931

[45] Date of Patent: Dec. 1, 1998

[54] 6,7-MODIFIED 11β-ARYL-4-OESTRENES

[75] Inventors: Eckhard Ottow; Wolfgang Schwede; Arwed Cleve; Walter Elger; Krzysztof Chwalisz; Martin Schneider, all of Berlin, Germany

[73] Assignee: Shering Aktiengesellschaft, Berlin, Germany

[21] Appl. No.: 78,290

[22] PCT Filed: Dec. 21, 1991

[86] PCT No.: PCT/EP91/02493

§ 371 Date: Oct. 27, 1993

§ 102(e) Date: Oct. 27, 1993

[87] PCT Pub. No.: WO92/11277

PCT Pub. Date: Jul. 9, 1992

[30] Foreign Application Priority Data

Dec. 22, 1990 [DE] Germany .......................... 40 42 007.8

[51] Int. Cl.⁶ .................. A61K 31/565; A61K 31/58; C07J 41/00; C07J 43/00
[52] U.S. Cl. .................. 514/173; 514/176; 514/177; 540/94; 540/107; 540/108; 540/114
[58] Field of Search .............. 540/94, 107, 108, 540/114; 514/173, 176, 177

[56] References Cited

U.S. PATENT DOCUMENTS 4,870,069  9/1989  Ottow et al. ........................... 514/179

FOREIGN PATENT DOCUMENTS

| | | |
|---|---|---|
| A-0190759 | 8/1986 | European Pat. Off. . |
| A-0277089 | 8/1988 | European Pat. Off. . |
| A-0404283 | 12/1990 | European Pat. Off. . |
| A-4018167 | 12/1991 | Germany . |
| A-4018168 | 12/1991 | Germany . |

*Primary Examiner*—Mark L. Berch
*Assistant Examiner*—Bruck Kifle
*Attorney, Agent, or Firm*—Millen, White, Zelano & Branigan, P.C.

[57] ABSTRACT

Compounds of the general formula I

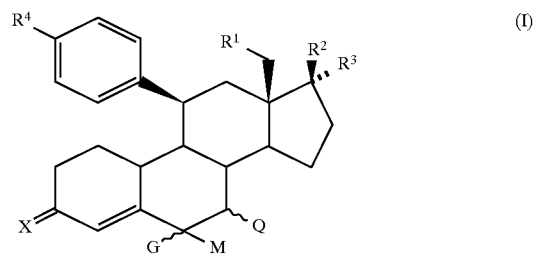

are described, in which x represents an oxygen atom or the hydroxyimino grouping >N~OH, $R^1$ represents a hydrogen atom or a methyl group, G represents a hydrogen atom, a halogen atom or a $C_1$–$C_4$-alkyl radical, when M and Q are hydrogen atoms or together are an additional bond, Q represents a $C_1$–$C_4$-alkyl radical when M and G are hydrogen atoms, or G and M together represent a methylene or ethylene group when Q is a hydrogen atom, and $R^2$, $R^3$ and $R^4$ have the meanings given in the description.

The novel compounds have pronounced antigestagenic and also antiglucocorticoid, antimineralocorticoid and antiandrogenic properties and are suitable for the preparation of medicaments.

4 Claims, No Drawings

6,7-MODIFIED 11β-ARYL-4-OESTRENES

The present invention relates to compounds of the general formula I (I)

in which
x represents an oxygen atom or the hydroxyimino grouping >N~OH,
$R^1$ represents a hydrogen atom or a methyl group,
$R^2$ represents a hydroxy group, a $C_1$–$C_{10}$-alkoxy group or a $C_1$–$Cl_{10}$-acyloxy group,
$R^3$ represents a hydrogen atom; the grouping —$(CH_2)_n$ $CH_2Z$ wherein $\underline{n}$ is 0, 1, 2, 3, 4 or 5 and Z represents a hydrogen atom, a cyano group or the radical —$OR^5$ in which $R^5$=H, $C_1$–$C_{10}$-alkyl or $C_1$–$C_{10}$-acyl; the grouping —$(CH_2)_m C\equiv C$-Y wherein $\underline{m}$ is 0, 1 or 2 and Y represents a hydrogen, fluorine, chlorine, bromine or iodine atom, or a $C_1$–$C_{10}$-hydroxyalkyl, $C_1$–$C_{10}$-alkoxyalkyl or $C_1$–$C_{10}$-acyloxyalkyl radical; or the grouping —$(CH_2)_p$—$CH=CH$—$(CH_2)_k CH_2 R^6$ wherein $\underline{p}$ is 0 or 1 and $\underline{k}$ is 0, 1 or 2 and $R^6$ represents a hydrogen atom, a hydroxy group, a $C_1$–$C_4$-alkoxy radical or a $C_1$–$C_4$-acyloxy radical, or alternatively $R^2$ and $R^3$ together represent a radical of the formula wherein $\underline{x}$=1 or 2, $R^4$ represents a hydrogen atom; a cyano group; a chlorine, fluorine, bromine or iodine atom; a trialkylsilyl group; a trialkylstannyl group; a straight-chain or branched, saturated or unsaturated, $C_1$–$C_8$-alkyl, -acyl or alkoxyalkyl radical; an amino group in which $R^7$ and $R^8$, each independently of the other, represents a hydrogen atom or a $C_1$–$C_4$-alkyl group; a corresponding amine oxide or the grouping —$OR^9$ or —$S(O)_i R^9$ in which $\underline{i}$=0, 1 or 2 and $R^9$ represents a hydrogen atom, a methyl, ethyl, propyl, isopropyl, methoxyphenyl, allyl or 2-dimethyl-aminoethyl group; or $R^4$ represents a heteroaryl radical of formula Iα

(Iα)

in which A represents a nitrogen, oxygen or sulphur atom, —B—D—E— represents the sequence of elements —C—C—C—, —N—C—C— or —C—N—C— and $R^{10}$ represents a hydrogen atom; a cyano group; a chlorine, fluorine, bromine or iodine atom; a trialkylsilyl group; a trialkylstannyl group; a straight-chain or branched, saturated or unsaturated $C_1$–$C_8$-alkyl, -acyl or alkoxyalkyl radical; an in which $R^7$ and $R^8$, each independently of the other, represents a hydrogen atom or a $C_1$–$C_4$-alkyl group; a corresponding amine oxide or the grouping —$OR^9$ or —$S(O)_i R^9$ in which $\underline{i}$=0, 1 or 2 and $R^9$ represents a hydrogen atom, a methyl, ethyl, propyl, isopropyl, methoxyphenyl, allyl or 2-dimethylaminoethyl group;

or $R^4$ represents a heteroaryl radical of formula Iβ

(Iβ)

in which A represents a nitrogen atom and —B—D—E— represents the sequence of elements —C—C—C—, —N—C—C—, —C—N—C— or —C—C—N— and $R^{10}$ has the meaning already given, or $R^4$ represents a phenyl radical of formula Iγ

(Iγ)

in which $R^{10}$ has the meaning already given, and
G represents a hydrogen atom, a halogen atom or a $C_1$–$C_4$-alkyl radical, when M and Q are hydrogen atoms or together are an additional bond,
Q represents a $C_1$–$C_4$-alkyl radical when M and G are hydrogen atoms, or G and M together represent a methylene or ethylene group when Q is a hydrogen atom, and the pharmacologically tolerable addition salts thereof with acids, to processes for their preparation, to pharmaceutical compositions containing those compounds, to their use for the manufacture of medicaments, and to the novel intermediates required therefor.

The invention relates especially to compounds in which X represents an oxygen atom.

The alkoxy, acyloxy, alkyl, acyl and hydroxyalkyl groups contained in $R^2$, $R^3$, $R^5$ and Y in the general formula I shall each have from 1 to 10 carbon atoms, and the alkoxyalkyl or acyloxyalkyl groups in Y shall each have from 2 to 10 carbon atoms. There may be mentioned as preferred alkoxy groups methoxy, ethoxy, propoxy and isopropoxy groups, and of the acyl(oxy) groups, formyl-(oxy), acetyl(oxy) and propionyl(oxy) are of particular importance.

The alkyl groups are especially methyl, ethyl, propyl, isopropyl and tert.-butyl groups and, of the hydroxyalkyl groups, the corresponding radicals substituted at any position by a hydroxy group are preferred.

There comes into consideration for $\underline{n}$ especially 0, 1, 2 or 3; when Z =CN, a cyanomethyl group ($\underline{n}$=0) is especially preferred. In addition to the groups already mentioned, Y may preferably also be a hydrogen, chlorine or bromine atom.

Of the alkenyl radicals in $R^3$, propenyl and butenyl groups, which may be present in the E- or $\underline{Z}$-configuration, are preferred, that is to say, when $R^3$ represents —($CH_2$)$_p$—CH=CH—($CH_2$)$_k$—$CH_2$—$R^6$ $\underline{k}$ shall preferably be 0 or 1 and p=0.

Of the alkoxy and acyloxy groups mentioned for $R^6$, which may be either straight-chain or branched, the methoxy, ethoxy, propoxy and isopropoxy, and the formyloxy, acetyloxy and propionyloxy groups, respectively, are especially preferred.

The $C_1$–$C_8$-alkyl and alkoxyalkyl radicals which $R^4$ may represent are especially the methyl, ethyl, propyl, isopropyl, cyclopentyl and cyclohexyl radical, and the alkoxymethyl or 1- or 2-alkoxyethyl groups containing the mentioned alkyl radicals; $R^4$ representing $C_1$–$C_8$acyl is especially acetyl, propionyl or isobutyryl.

If $R^4$ represents the amino group

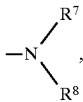

then $R^7$ and $R^8$ preferably each represent a methyl radical, or the ethyl radical is also especially important, in which case either each of the radicals at the nitrogen atom represents an ethyl radical, or one represents a methyl radical and one an ethyl radical.

For the substituent $R^9$ attention is drawn especially to the methyl, ethyl and 2-(dimethylamino)-ethyl group.

Of the heteroaryl radicals possible in accordance with formula Iα, 3-thienyl, 3-furyl and 3-pyrrolyl are preferred in which $R^{10}$ represents a cyano, methoxy or dimethylamino group.

As heteroaryl radicals of formula Iβ there come into consideration in accordance with the invention especially 3- or 4-pyridyl, 5-pyrimidinyl, 4-pyridazinyl or pyrazinyl radicals. The phenyl radical of formula Iγ contains as substituent $R^{10}$ especially the cyano, methoxy or dimethylamino group, these substituents preferably being in the p-position of the phenyl ring.

G representing a halogen atom shall be especially the chlorine atom and representing a $C_1$–$C_4$-alkyl radical especially the methyl group.

Q representing a $C_1$–$C_4$-alkyl radical shall preferably be the methyl or ethyl group.

G and M shall together preferably be a methylene group.

The following compounds are especially preferred in accordance with the invention:

17β-hydroxy-11β-(4-methoxyphenyl)-17α-(prop-1-ynyl)-4,6-oestradien-3-one

17β-hydroxy-11β-(4-methoxyphenyl)-7β-methyl-17α-(prop-1-ynyl)-4-oestren-3-one

17β-hydroxy-11β-(4-methoxyphenyl)-7α-methyl-17α-(prop-1-ynyl)-4-oestren-3-one

11β-[4-(3-acetylphenyl)-phenyl]-17β-hydroxy-17α-(prop-1-ynyl)-4,6-oestradien-3-one 11β-(4-acetylphenyl)-17β-hydroxy-17α-(prop-1-ynyl)-4,6-oestradien-3-one 11β-(4-acetylphenyl)-17β-hydroxy-17α-(3-hydroxyprop-1(Z)-enyl)-6β-methyl-4-oestren-3-one 11β-(4-acetylphenyl)-17β-hydroxy-17α-(3-hydroxyprop-1(Z)-enyl)-6α-methyl-4-oestren-3-one 17β-hydroxy-17α-(3-hydroxyprop-1(Z)-enyl)-6β-methyl-11β-[4-(3-pyridyl)-phenyl]-4-oestren-3-one 17β-hydroxy-17α-(3-hydroxyprop-1(Z)-enyl)-6α-methyl-11β-[4-(3-pyridyl)-phenyl]-4-oestren-3-one 17β-hydroxy-17α-(3-hydroxyprop-1-ynyl)-6β-methyl-11β-[4-(3-pyridyl)-phenyl]-4-oestren-3-one 6β-bromo-11β-(4-dimethylaminophenyl)-17β-hydroxy-17α-(prop)-1-ynyl)-4-oestren-3-one 6β-bromo-11β-(3-bromo-4-dimethylaminophenyl)-17β-hydroxy-17α-(prop)-1-ynyl)-4-oestren-3-one 11β-(4-dimethylaminophenyl)-17β-hydroxy-17α-(prop-1-ynyl)-4,6-oestradien-3-one 11β-(4-dimethylaminophenyl)-17α-ethynyl-17α-hydroxy-4,6-oestradien-3-one 11β-(3-bromo-4-dimethylaminophenyl)-17β-hydroxy-17α-(prop-1-ynyl)-4,6-oestradien-3-one 11β-[4-(4-cyanophenyl)-phenyl]-17β-hydroxy-17α-(prop-1-ynyl)-4,6-oestradien-3-one 11β-[4-(4-cyanophenyl)-phenyl]-17β-hydroxy-17α-(3-hydroxyprop-1-ynyl)-4,6-oestradien-3-one 11β-[4-(4-cyanophenyl)-phenyl]-17β-hydroxy-17α-(3-hydroxyprop-1(Z)-enyl)-4,6-oestradien-3-one 17β-hydroxy-11β-[4-(4-methylthiophenyl)-phenyl]-17α-(prop-1-ynyl)-4,6-oestradien-3-one 17β-hydroxy-17α-(3-hydroxyprop-1-ynyl)-11β-[4-(4-methyl-thiophenyl)-phenyl]-4,6-oestradien-3-one 17β-hydroxy-17α-(3-hydroxyprop-1(Z)-enyl)-11β-[4-(4-methylthiophenyl)-pheny]-4,6-oestradien-3-one 17β-hydroxy-11β-[4-(4-methylsulphinylphenyl)-phenyl]-17α-(prop-1-ynyl)-4,6-oestradien-3-one 17β-hydroxy-11β-[4-(4-methylsulphonylphenyl)-phenyl]-17α-(prop-l-ynyl)-4,6-oestradien-3-one 11β-[4-(4-acetylphenyl)-phenyl]-17β-hydroxy-17α-(3-hydroxyprop-1(Z)-enyl)-4,6-oestradien-3-one 17β-hydroxy-11β-[4-(3-furanyl)-phenyl]-6β-methyl-17α-(3-hydroxyprop-1(Z)-enyl)-4-oestren-3-one 17β-hydroxy-11β-[4-(3-furanyl)-phenyl]-6α-methyl-17α-(3-hydroxyprop-1(Z)-enyl)-4-oestren-3-one 11β-[4-(3-furanyl)-phenyl]-17β-hydroxy-17α-(prop-1-ynyl)-4,6-oestradien-3-one 17β-hydroxy-6β-methyl-17α-(3-hydroxyprop-1(Z)-enyl)-11β-[4-(3-thienyl)-phenyl]-4-oestren-3-one 17β-hydroxy-6α-methyl-17α-(3-hydroxyprop-1(Z)-enyl)-11β-[4-(3-thienyl)-phenyl]-4-oestren-3-one 17β-hydroxy-6β-methyl-17α-(3-hydroxyprop-1(Z)-enyl)-11β-[4-(2-thiazolyl)-phenyl]-4-oestren-3-one 17β-hydroxy-6α-methyl-17α-(3-hydroxyprop-1(Z)-enyl)-
11β-[4-(2-thiazolyl)-phenyl]-4-oestren-3-one
17β-hydroxy-11β-[4-(5-pyrimidinyl)-phenyl]-6β-methyl-
17α-(3-hydroxyprop-1-(Z)-enyl)-4-oestren-3-one
17β-hydroxy-11β-[4-(5-pyrimidinyl)-phenyl]-6α-methyl-
17α-(3-hydroxyprop-1-(Z)-enyl)-4-oestren-3-one
17β-hydroxy-11β-[4-(5-pyrimidinyl)-phenyl]-6β-methyl-
17α-(prop-1-ynyl)-4-oestren-3-one
17β-hydroxy-17α-(prop-1-ynyl)-11β-[4-(5-pyrimidinyl)-
phenyl]-4,6-oestradien-3-one
17α-cyanomethyl-17β-hydroxy-11β-(4-hydroxyphenyl)-4,
6-oestradien-3-one
11β-(4-acetylphenyl)-17α-cyanomethyl-17β-hydroxy-4,6-
oestradien-3-one
17α-cyanomethyl-17β-hydroxy-11β-[4-(2-propenyl)-
phenyl]-4,6-oestradien-3-one
17α-cyanomethyl-17β-hydroxy-11β-[4-(4-
methylthiophenyl)-phenyl]-4,6-oestradien-3-one The compounds of the general formula I are competitive antagonists of progesterone (antigestagens). All steroidal antigestagens known until recently comprise, in addition to a $\Delta^4\Delta^9$-3-oxo-chromophor, a preferably substituted 11β-phenyl radical [A. Belanger, D. Philibert and G. Teutsch, Steroids 37, 2742 (1981); D. Philibert, T. Ojasoo and J. P. Raynand, Endocrinology 10, 1850 (1977), EP-A 057 115; G. Teutsch, T. Ojasoo and J. P. Raynand, J. Steroid Biochem, 31, 549 (1988)].

Antigestagens of steroidal origin in which in place of the 9,10-double bond there is a methylene bridge between the 9-C-atom and one of the ortho-C-atoms of the 11β-aryl ring have also been discovered recently (EP-A 0283428). Clearly, the introduction of the 11β-aryl radical causes the change from gestagenic to antigestagenic activity. However, it has not so far been possible to produce an antigestagen closest to progesterone, that is to say "an antiprogesterone", that would have no 9,10 double bond but that in addition to an 11β-aryl radical would contain a "free" 10β-substituent, for example a hydrogen atom. Attempts to isomerise 11β-[4-(substituent)-aryl]-17β-hydroxy-5(10)-oestren-3-one to form the corresponding compound having a 4(5) double bond by means of brief treatment with dilute mineral acids, conditions under which in the 11-unsubstituted series a double bond displacement from the 5(10) to the 4(5) position takes place readily, have met with failure [G. Neef, G. Sauer and R. Wiechert, Tet. Let., 24, 5205 (1983)].

11β-4-aryl-oestrenes were described for the first time in German Patent Application P 39 21 059.6.

The preparation of the compounds of the general formula I according to the invention is reproduced in the following reaction scheme:

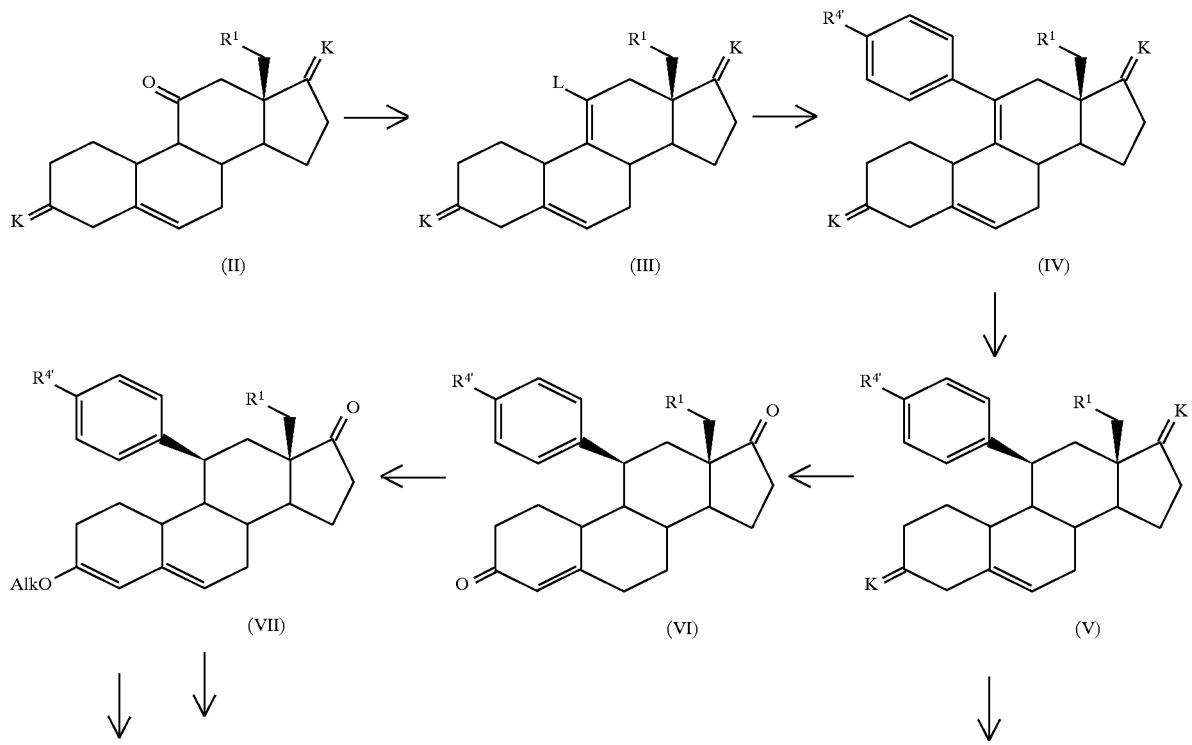

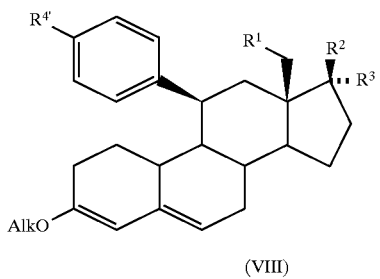 (VIII)

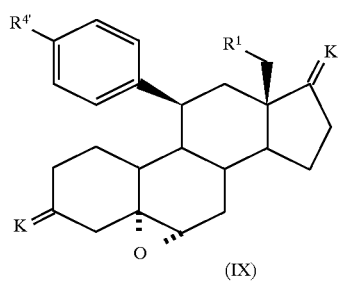 (IX)

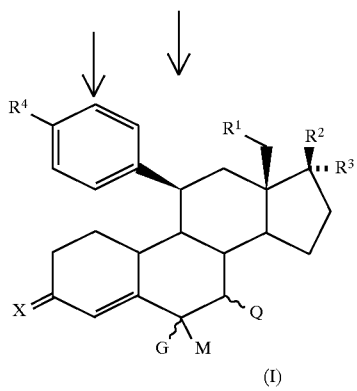 (I)

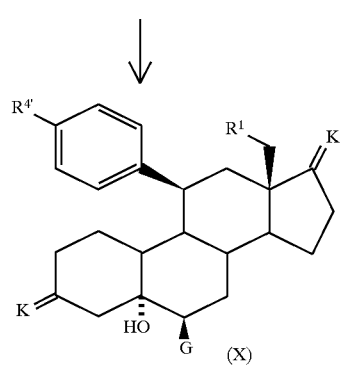 (X)

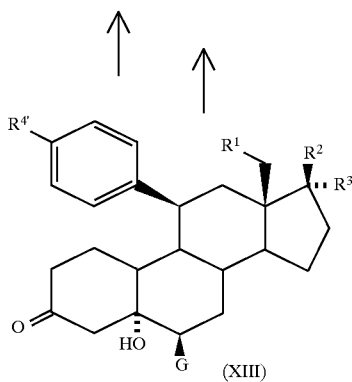 (XIII)

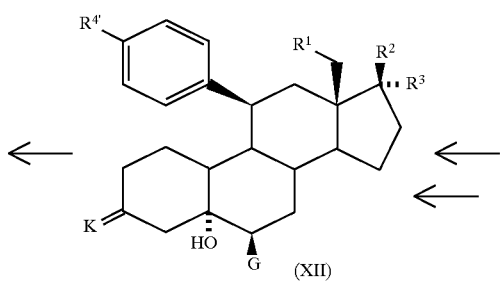 (XII)

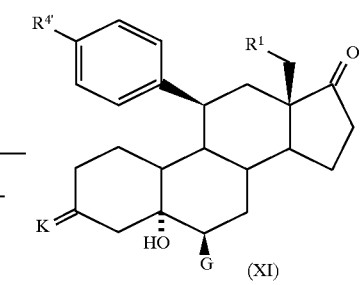 (XI)

K=

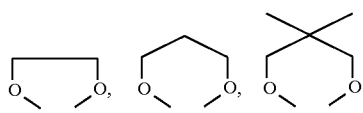

or other oxygen ketals

Alk=C$_1$–C$_4$Alkyl

In accordance with the present invention, compound II [Recl. Trav. Chim. Bays-Pas 107, 331, (1988)] is first converted into a compound of formula III wherein L represents a perfluoroalkylsulphonyloxy group C$_n$F$_{2n+1}$SO$_2$O-(n= 1, 2, 3 or 4).

Compound III is reacted, in the presence of a catalytic amount of a transition metal catalyst, with an aryl compound of the general formula Z

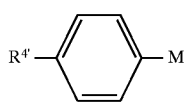 (Z)

in which M represents one of the radicals:

| —B(alkyl)$_2$ | |
|---|---|
| —Sn(alkyl)$_3$ | alkyl = C$_1$–C$_4$alkyl |
| —B(OH)$_2$ | |
| —ZnHal | Hal = Cl, Br, I, |
| —MgHal | | and R$^{4'}$ represents one of the radicals mentioned for R$^4$, to form a compound of the general formula IV wherein R$^1$ has the meaning given in formula I and R$^{4'}$ has the meaning given in formula Z and optionally, if R$^{4'}$ in formula I is to have a different meaning from R$^{4'}$ in formula IV, a compound of the general formula IV in which R$^{4'}$ represents a bromine atom or, after conversion of a methoxy group representing R$^{4'}$, a perfluoroalkylsulphonyloxy group C$_n$F$_{2n+1}$SO$_2$O- (n=1, 2, 3 or 4), is reacted with a compound of the general formula W

R$^4$—M     (W)

in which R$^4$ has the meaning finally desired for that substituent in formula I and M has the meaning already given in formula Z.

L in compound III preferably represents the trifluoromethylsulphonyloxy group. The transition metal catalyst used according to the Examples of the present invention for coupling the aryl compound of the general formula Z with the compound containing the leaving group L is palladium tetrakistriphenylphosphine (see literature indicated below); nickel tetrakistriphenylphosphine or similar such transition metal catalysts could equally be used.

The variant that the ultimately desired substituent $R^4$ is introduced by the functionalisation of a bromine or methoxy substituent $R^{4'}$ in compound IV is selected when the aryl compound of the general formula Z to be coupled, in which $R^{4'}$ is already identical to $R^{4'}$, is not available or is not suitable for the coupling. Transition metal-catalysed aryl coupling reactions of compounds of the general formula Z-type with compounds carrying a leaving group are described, for example, in: —Sn(alkyl)$_3$-substituted aromatic compounds: J. E. McMurry and S. Mohanraj, Tetrahedron Letters, 24, No. 27, pages 2723–2726, (1983); X. Lu and J. Zhu, Communications, pages 726–727, (1987); Q. -Y. Chen and Z. -Y. Yang, Tetrahedron Letters 27, No. 10, pages 1171–1174, (1986); S. Cacchi, P. G. Ciattini, E. Morera and G. Ortar, Tetrahedron Letters 27, No. 33, pages 3931–3934, (1986); A. M. Echavarren and J. K. Stille, J. Am. Chem. Soc. (1987), 109, pages 5478–5486 and J. Am. Chem. Soc. (1988), 110, page 1557; —B(OH)$_2$— and —B(Oalkyl)$_2$-substituted aromatic compounds: Y. Hoshino, N. Miyaura and A. Suzuki, Bull. Chem. Soc. Jpn. 61, 3008 (1988); H. Matsubasa, K. Seto, T. Tahara and S. Takahashi; Bull. Chem. Soc. Jpn, 62, 3896 (1989); —ZnCl-substituted aromatic compounds: R. McCague, Tet. Lett., 28, 701 (1987); A. Arcadi, A. Burini, S. Cacchi, M. Delmastro, F. Marinelli, D. Pietroni, Syn. Les., 1, (1990), page 47.

The compounds of the general formula V, which are suitable as starting materials for the preparation of the 10β-H-steroids of the general formula I, can readily be prepared by reducing a compound of formula IV, wherein $R^{4'}$ and $R^1$ have the meanings given in the formulae, without destruction of the aromatic system and the 5,6-double bond, to a compound of the general formula V in which $R^4$ and $R^1$ have the meanings already given. On the reduction of IV, the 11β-aryl compound V is formed (stereoselective reduction).

Various methods are suitable in accordance with the invention for reducing the 9(11)-double bond in IV: preferred in accordance with the invention is reduction with an electropositive metal in an electron-solvating solvent or in a solvent containing a solubiliser. There comes into consideration as electron-solvating solvent especially ammonia.

Equimolar amounts of reducing agent are sufficient for the reduction, but it is also possible for a substantial excess of reducing agent to be used without the aromatic system and/or the 5,6-double bond being attacked.

Any metal suitable for a Birch reduction may be used as the electropositive metal. Preferred in accordance with the invention are lithium, potassium, sodium and calcium, with lithium being especially preferred.

The compounds of the general formula V may then be further processed by a number of different methods depending on the desired final compound of the general formula I.

Firstly, the diketal compound V may be converted by treatment with a strong acid into the corresponding 3,17-diketone of the general formula VI.

From that a dienol ether of the general formula VII (Alk=$C_1$–$C_4$alkyl) is then produced according to current methods (see experimental section).

The dienol ether VII acts as a substrate for the introduction of the substituents $R^2$ and $R^3$ desired at the C-17-atom.

This introduction is carried out analogously to processes known from the literature (e.g. J. Fried, J.A. Edwards, "Organic Reactions in Steroid Chemistry", Van Nostrand Reinhold Company, 1972, Vol. 1 and 2; "Terpenoids and Steroids", Specialist Periodical Report, The Chemical Society, London, Vol. 1–2) by nucleophilic addition to the C-17-ketone.

The introduction of the substituent —C≡C—Y as $R^3$, Y having the meaning given above, is carried out with the aid of a metallated compound of the general formula MC≡C—Y' in which Y' is an alkyne-protecting group, such as, for example, trimethylsilyl or tert.-butyldimethylsilyl.

The organometallic compound can also be formed in situ and caused to react with the 17-ketone. For example, acetylene and an alkali metal, especially potassium, sodium or lithium, can be allowed to act on the 17-ketone in a suitable solvent in the presence of an alcohol or in the presence of ammonia. The alkali metal may also be in the form of, for example, methyl- or butyl-lithium. Suitable solvents are especially dialkyl ethers, tetrahydrofuran, dioxan, benzene and toluene.

The introduction of 3-hydroxypropyne or 3-hydroxypropene in the 17-position is effected by reacting the 17-ketone with the dianion of propargyl alcohol (3-hydroxypropyne), for example the propargyl alcohol dipotassium salt produced in situ, to form the 17α-(3-hydroxyprop-1-ynyl)-17β-hydroxy derivative, or with metallated derivatives of 3-hydroxypropyne, for example 1-lithium-3-(tetrahydropyran-2'-yloxy)-prop-1-yn-1-ide, to form the 17-[3-(tetrahydropyran-2'-yloxy)-prop-1-ynyl]-17β-hydroxy derivative, which can then be hydrogenated to the 17-(3-hydroxypropyl or hydroxypropenyl)-17β-hydroxy compounds. This is effected, for example, by hydrogenation at room temperature and normal pressure in solvents such as methanol, ethanol, propanol, tetrahydrofuran (THF) or ethyl acetate with the addition of noble metal catalysts, such as platinum or palladium.

Homologous hydroxyalkyne, hydroxyalkene and hydroxy-alkane groups are introduced in a corresponding manner with homologues of propargyl alcohol.

The compound with the Z-configured double bond in the hydroxypropenyl group is produced by hydrogenating the acetylenic triple bond with a deactivated noble metal catalyst [J. Fried, J. A. Edwards: Organic Reactions in Steroid Chemistry, Van Nostrand Reinhold Company (1972), page 134; and H.O. House: Modern Synthetic Reactions (1972), page 19]. There come into consideration as deactivated noble metal catalysts, for example, 10% palladium-on-barium sulphate in the presence of an amine or 5% palladium-on-calcium carbonate with the addition of lead (II) acetate. The hydrogenation is discontinued after one equivalent of hydrogen has been taken up.

The compound with the E-configured double bond in the hydroxypropenyl group is produced by reducing the acetylenic triple bond in a manner known per se. Numerous methods of converting alkynes into trans-olefins are described in the literature, for example reduction with sodium in liquid ammonia [J. Am. Chem. Soc. 63 (1941) 216], with sodium amide in liquid ammonia [J. Chem. Soc. (1955), 3558], with lithium in low-molecular amines [J. A. Chem. Soc. 77 (1955) 3378], with boranes [J. Am. Chem. Soc. 93 (1971) 3395 and 94 (1972) 6560], with diisobutylaluminium hydride and methyllithium [J. Am. Chem. Soc. 89 (1967) 5085] and especially with lithium aluminium hydride/alcoholate [J. Am. Chem. Soc. 89 (1967) 4245]. A further possibility is reduction of the triple bond with chromium(II) sulphate in the presence of water or dimethylformamide in weakly acidic medium [J. Am. Chem. Soc. 86 (1964) 4358] and, generally, reduction by the action of transition metal compounds alternating with an oxidation step.

The introduction of hydroxyalkenes can also be carried out directly, by adding a corresponding metallated hydroxyalkenyl compound, such as, for example, 1-lithium-3-(tetrahydropyran-2'-yloxy)-prop-1($\underline{E}$)-ene (J. Org. Chem. 40 2265) or 1-lithium-3-(tetrahydropyran-2'-yloxy)-prop-1($\underline{Z}$)-ene (Synthesis 1981, 999). Homologues can also be introduced in that manner.

The introduction of 3-hydroxypropane in the 17-position can also be carried out directly, by reacting the 17-ketone with metallated derivatives of 3-halopropanols— the hydroxy group in the metallisation step being in the form of an alcoholate [Tetrahedron Letters (1978), 3013] or in the form of a protected function [(J. Org. Chem. 37, (1947)]—to form the 17-(3-hydroxypropyl)-17β-hydroxy compound or the compound protected at the terminal hydroxy group, respectively. There come into consideration as protecting groups, for example, ethoxy-ethyl, tetrahydropyranyl and methoxymethyl groups.

If end products of formula I are desired in which $R^2/R^3$ represent

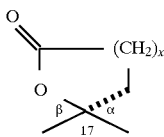

$\underline{x}$=1 or 2, the 17-(3-hydroxypropyl) or 17-(4-hydroxybutyl) compound is oxidised in a manner known per se, for example with Jones' reagent, pyrolusite, pyridinium dichromate, pyridinium chlorochromate, chromic acid/ pyridine or the fetizone reagent silver carbonate/Celite [Compt. rend. 267 (1968) 900].

The preparation of end products of formula I in which $R^2/R^3$ represent

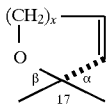

$\underline{x}$ =1 or 2is carried out by a ring closure reaction of the corresponding 17-(3-hydroxyprop-1-($\underline{Z}$)-enyl- or 17-(4-hydroxybut-1-($\underline{Z}$)-enyl-17-β-hydroxy educt. Hydrogenation of the unsaturated 5- or 6-ring-spiro ether with palladium/ activated carbon contact results in the saturated spiro ethers.

The introduction of the 17-cyanomethyl side chain is effected in a manner known per se from the 17-ketone, for example by way of the 17-spiro epoxide and cleavage of the spiro epoxide with HCN according to Z. [Chem. 18 (1978) 259–260 ].

The introduction of the 17-hydroxyacetyl side chain is also carried out according to methods known per se, for example according to the methods described in J. Org. Chem. 47 (1982), 2993–2995, Chem. Ber. 113 (1984), 1184 and U.S. Pat. No. 4,600,538.

Starting from the compound of the general formula VIII containing the side chains, the 6,7-double bond is then introduced in addition to the 3,4-double bond by dienol ether bromination and subsequent hydrogen bromide removal [J. Fried, J. A. Edwards, Organic Reactions in Steroid Chemistry, Van Nostrand Reinhold Company 1972, pages 265–374; Tetrahedron 42, (1986) 2971].

The dienol ether bromination is carried out, for example, analogously to the directions in Steroids I, 233.

The hydrogen bromide removal to form the $\Delta^6$-double bond is carried out by heating the 6-bromine compound with basic agents, preferably with lithium bromide and lithium carbonate or with lithium bromide and calcium carbonate in an aprotic solvent, such as dimethylformamide, at temperatures of from 50° to 120° C. Another possible method of removing HBr comprises heating the 6-bromine compound in collidine or lutidine.

The introduction of a 6-methylene group may be carried out, for example using a 3-amino-3(4),5(6)-diene derivative as starting material, by reaction with formalin in alcoholic solution [Helv. Chim. Acta. 56 (1973) 2396] to form the 6α-hydroxymethyl group, and subsequent removal of water by acid means, for example with hydrochloric acid in dioxan/water, or using a 3-alkoxy-3(4),5(6)-diene derivative as starting material and proceeding analogously to the method described in U.S. Pat. No. 4,544,555, or may be carried out directly, using a 3-oxo-4(5)-ene derivative as starting material and proceeding analogously to the directions in Synthesis (1982) 34.

Compounds alkylated in the 7-position are obtained by 1,6-addition to the corresponding enones according to known methods [J. Fried, J. A. Edwards; Organic Reactions in Steroid Chemistry, Van Nostrand Reinhold Company 1972, page 75 to 82, 2; and J. Am. Chem. Soc. 99 (1977) 1673].

Alternatively it is possible for the further processing to epoxidise the intermediate compounds of the general formula V, for example using organic per-acids or in the presence of hexachloroacetone or nitrotrifluoroacetophenone. The resulting epoxides of the general formula IX may then be opened using complex hydrides or a compound GMgHal (G=$C_1$–$C_4$alkyl, Hal=halogen), a compound of the general formula X being obtained.

The next reaction step serves to introduce the substituent $R^4$ or $R^{4'}$ in the $\underline{p}$-position on the 11β-phenyl ring.

This procedure is necessary when $R^4$ is not introduced directly during coupling of the compound III with the aryl compound Z to form compound IV.

There is used as starting material for this introduction compound X wherein $R^4$=OH, which is obtainable from the corresponding methoxy compound by ether cleavage, for example with sodium ethanethiolate in a solvent, such as dimethylformamide.

By reacting the hydroxy compound with a perfluoro-($C_1$–$C_4$)-alkylsulphonic acid anhydride or halide in the presence of a base, such as pyridine or 4-(dimethyl-amino)-pyridine, the corresponding 11β-[4-(perfluoro-alkylsulphonyloxy) phenyl] compound is obtained [P.J. Stang, M. Hanack and L. R. Subramanian, Synthesis 85, (1982)].

In the subsequent coupling of the 11β-aryl compound with $R^{4''}$-Sn(Alkyl)$_3$ or $R^{4''}$-BL$_2$, the procedure is either that in a transition metal-catalysed reaction (preferably Pd°) the perfluoroalkyl sulphonate leaving group is displaced with essentially almost simultaneous substitution by the desired substituent or a precursor thereof (Aryl couplings with tin compounds: J. E. McMurry and S. Mohanraj, Tetrahedron Letters, 24, No. 27, pages 2723–2726, (1983); X. Lu and J. Zhu, Communications, pages 726–727, (1987); Q. -Y. Chen and Z. -Y. Yang, Tetrahedron Letters, 27, No. 10, pages 1171–1174, (1986); S. Cacchi, P.G. Ciattini, E. Morera and G. Ortar, Tetrahedron Letters 27, No. 33, pages 3931–3934, (1986); A. M. Echavarren and J. K. Stille, J. Am. Chem. Soc. (1987), 109, pages 5478–5486; with boron compounds : Synthesis 936 (1984), Chem. Pharm. Bull. 33, 4755–4763

(1985); J.Org.Chem. 49, 5237–52433 (1984); Bull. Chem. Soc. Jpn. 61, 3008–3010 (1988)) or that there is produced as intermediate from the perfluoroalkyl sulphonate compound with transition metal catalysis a corresponding tri-organylstannyl, preferably tri-n-alkylstannyl, compound [J. K. Stille, Angew. Chem. 98 (1986), pages 504–519]. This is then reacted in a one-pot reaction with a halogen-substituted, preferably a bromine- or iodine-substituted, carbocyclic or heterocyclic aromatic compound [Y. Yamamoto, Y. Azuma, H. Mitoh, Communications, pages 564–565, (1986); T.J. Bailey, Tetrahedron Letters, 27, No. 37, pages 4407–4410, (1986)], which, if desired, may in addition carry further substituents; the 1β-phenyl radical then has the desired substitution or a precursor to the desired substitution.

Numerous such reactions with steroids in which a trifluoromethanesulphonate group is located in the 4-position of an 11β-phenyl ring are described in EP-A-0283428.

Then, the 17-ketal is selectively cleaved to the 17-ketone (general formula XI) with a weak acid (oxalic acid) and the C-17 side chains are introduced in the manner already described hereinbefore. The mentioned selective ketal cleavage can also be carried out at the triflate stage and the triflate further processed to the 17-ketone stage.

In the compound of the general formula XII obtained after the introduction of the side chains the 3-keto-protecting group is then removed under mild acidic conditions (acetic acid or 4N hydrochloric acid at 0° C.).

The 3-keto-4-ene compounds of the general formula I with substituent G in the β-configuration are obtained by treating the resulting compounds of the general formula XIII with dilute aqueous sodium hydroxide solution, whilst if the compounds XIII are reacted with aqueous hydrochloric acid (or another strong acid) the corresponding compounds of the general formula I in which the substituent G is in the α-configuration are formed.

Free hydroxy groups may be alkylated or acylated in a manner known per se.

If desired, it is also possible to introduce the substituent $R^4$ first and then introduce the substituents $R^2$ and $R^3$, depending upon whether the process conditions of the second reaction step adversely affect the substituents first introduced or built on. In principle it is possible for all or part of the p-substituent on the 11β-phenyl radical to be introduced at any reaction step from compound IV.

Any protecting groups still present are removed according to current methods.

The resulting compounds of the general formula I in which X represents an oxygen atom can, if desired, be converted into the oximes (formula I in which X represents the hydroxyimino grouping >N~OH, wherein the hydroxy group may be in the syn- or anti-configuration) by reaction with hydroxylamine hydrochloride in the presence of tertiary amines at temperatures of from −20° to +40° C. Suitable tertiary bases are, for example, trimethylamine, triethylamine, pyridine, N,N-dimethylaminopyridine, 1,5-diazabicyclo[4.3.0]non-5-ene (DBN) and 1,8-diazabicyclo-[5.4.0]undec-7-ene (DBU), with pyridine being preferred.

The removal of the 3-oxo group to form an end product of the general formula I in which X represents 2 hydrogen atoms can be carried out, for example, according to the directions given in DE-A-2805490 by reductive cleavage of the thioketal.

The novel compounds of the general formula I and their addition salts with pharmaceutically tolerable acids are valuable pharmaceutical agents. They exhibit a strong affinity for the gestagen receptor and surprisingly have pronounced antigestagenic and antiglucocorticoid, antimineralocorticoid and antiandrogenic properties. These important biological activities can be used for medicinal purposes.

Active substances of this kind having pronounced antigestagenic activity are suitable for inducing abortion since they displace from the receptor the progesterone necessary for maintaining the pregnancy. They are therefore valuable and of interest in view of their use for post-coital fertility control.

The novel compounds can furthermore be used for treating endometriosis. They can also be employed to treat hormone irregularities, trigger menstruation and induce birth. In addition they can be used for the treatment of hormone-dependent carcinomas.

The compounds of the general formula I according to the invention and their addition salts with pharmaceutically tolerable acids also exhibit an antiglucocorticoid activity and can therefore also be used as medicaments for the treatment of corticoid-induced disorders (glaucoma) and to control side-effects that arise in the case of long-term treatment with glucocorticoids (Cushing's syndrome). They therefore also make it possible to control disorders attributable to a supersecretion of glucocorticoids, especially adiposity, arteriosclerosis, hypertension, osteoporosis, diabetes and insomnia.

The compounds of the general formula I according to the invention and their addition salts with pharmaceutically tolerable acids having antiandrogenic activity can be used in the treatment of hypertrophy and carcinomas of the prostate. They also render possible a specific treatment of androgenisation phenomena in women: pathological hairiness in hirsutism, androgenetic alopecia, and the increased sebaceous gland function in acne and seborrhoea can be favourably influenced.

The invention thus also relates to medicaments based on compounds of the general formula I and their addition salts with pharmaceutically tolerable acids, optionally together with customary excipients and carriers.

The compounds according to the invention and salts thereof can be processed according to methods of galenical pharmacy that are known per se into pharmaceutical compositions for enteral, percutaneous, parenteral or local administration. They can be administered in the form of tablets, dragrees, gelatin capsules, granules, suppositories, implants, injectable sterile aqueous or oily solutions, suspensions or emulsions, ointments, creams and gels. The active ingredient or ingredients may be mixed with excipients customary in galenical pharmacy, such as, for example, gum arabic, talc, starch, mannitol, methylcellulose, lactose, surfactants such as Tweens® or Myrj®, magnesium stearate, aqueous or non-aqueous carriers, paraffin derivatives, wetting agents, dispersing agents, emulsifying agents, preservatives and flavourings for taste correction (for example ethereal oils).

The invention therefore also relates to pharmaceutical compositions that comprise as active ingredient at least one compound according to the invention or one of its addition salts with pharmaceutically tolerable acids. There may be mentioned as addition salts of the products according to the invention with acids especially the hydrochlorides and the methanesulphonates. One unit dose contains approximately 1–100 mg of active ingredient(s).

The dose of the compounds according to the invention for humans is approximately 1–1000 mg per day.

The following Examples serve to illustrate the invention in more detail:

EXAMPLE 1

17β-Hydroxy-11β-(4-methoxyphenyl)-17α-(prop-1-ynyl)-4,6-oestradien-3-one a) 3,3;17,17-Bis-(ethylenedioxy)-11-trifluoromethylsulphonyloxy-5,9(11)-oestradiene 26.1 g (69.7 mmol) of 3,3;17,17-bis-(ethylenedioxy)-5-oestren-11-one are dissolved in 350 ml of absolute methylene chloride and, under an inert gas, 18 ml of 2,6-di-tert.-butylpyridine are added. After this solution has been cooled to 0° C., 12.9 ml (76.8 mmol) of trifluoromethanesulphonic acid anhydride are slowly added dropwise. The reaction mixture is then stirred for 20 hours at room temperature. In order to work up, the mixture is poured onto saturated sodium hydrogen carbonate solution, the organic phase is removed and the aqueous phase is then extracted with methylene chloride. The combined organic phases are washed with saturated sodium chloride solution, dried over sodium sulphate and concentrated in vacuo. Chromatography of the crude product on silica gel with a mixture of ethyl acetate/hexane yields, in addition to 16.4 ml of 2,6-di-tert.butylpyridine and 5.1 g of 3,3;17,17-bis-(ethylenedioxy)-5-oestren-11-one, 27 g of 3,3;17,17-bis-(ethylenedioxy)-11-trifluoromethylsulphonyloxy-5,9(11)-oestradiene in the form of a white foam.

Method 2

1.52 g of 3,3;17,17-bis-(ethylenedioxy)-11-trifluoromethylsulphonyloxy-5, 9(11)-oestradiene are dissolved in 25 ml of absolute dimethylformamide and 270 mg of lithium chloride and 350 mg of tetrakistriphenylphosphinepalladium are added. After the reaction mixture has been stirred for 5 minutes, 1.3 ml of tri-n-butyl-4-methoxyphenyltin are added and the whole is stirred for 3 hours at 110° C. under an inert gas, cooled to room temperature and diluted with ethyl acetate. After filtration through Celite and after the filtration residue has been washed with ethyl acetate, the organic phase is washed with saturated sodium chloride solution, dried over sodium sulphate and concentrated in vacuo. Chromatography of the residue on aluminium oxide (neutral, stage III) with a mixture of ethyl acetate/hexane yields 1.15 g of 3,3;17,17-bis-(ethylenedioxy)-11-(4-methoxyphenyl)-5,9(11)-oestradiene in the form of a white foam.

By way of example, the preparation of some other products analogously to the above methods 1) or 2) is detailed in the following Table:

| | Aromatic compound | Product | Yield [%] | Physical data |
|---|---|---|---|---|
| a) | 4-methoxy phenylboronic acid or | 3,3;17,17-bis-(ethylenedioxy)-11-(4-methoxyphenyl)-5,9(11)-oestradiene | 97 | M.p. = 156° C. (diisopropyl ether) $[\alpha]_D^{20} = -0.1°$ (CHCl$_3$; c = 0.52) |
| b) | tri-n butyl-4-methoxyphenyltin | | 83 | |
| a) | 4-methylphenyl-boronic acid | 3,3;17,17-bis(ethylenedioxy)-11-(4-methylphenyl)5,9(11)-oestradiene | 92 | M.p. = 175° C. (diisopropyl ether) $[\alpha]_D^{20} = -11°$ (CHCl$_3$; c = 0.505) |
| a) | phenylboronic acid | 3,3;17,17-bis-(ethylenedioxy)-11-phenyl-5,9(11)-oestradiene | | M.p. = 189° C. (diisopropyl ether) $[\alpha]_D^{20} = -3°$ (CHCl$_3$; c = 0.5) |
| a) | 4-bromophenyl-boronic acid | 3,3;17,17-bis-(ethylenedioxy)-11-(4-bromophenyl)-5,9(11)-estradiene | 62 | M.p. = 171° C. (diisopropyl ether) $[\alpha]_D^{20} = -15°$ (CHCl$_3$; c = 0.5) |

$[\alpha]_D^{20}$=+104° (CHCl$_3$; c=0.505)

$^1$H-NMR (CDCl$_3$) δ [ppm]: 5.58 (1H, d broad J=5 Hz, H-6); 3.7–4.0 (8H, m, H-ketals); 2.88 (1H, d broad J=11Hz, H- 10); 2.74 (1H, dtr J=16 Hz and J=2.5 Hz, H-12); 2.18–2.33 (2H, m, H-4); 0.84 (3H, s, H-18).

b) 3,3;17,17-Bis-(ethylenedioxy)-11-(4-methoxyphenyl)-5, 9(11)-oestradiene

Method 1

21.6 g (42.6 mmol) of 3,3;17,17-bis-(ethylene-dioxy)-11-trifluoromethylsulphonyloxy-5, 9(11)-oestradiene are dissolved in a mixture of 360 ml of toluene and 170 ml of ethanol, and 2.5 g of palladium tetrakistriphenylphosphine, 3.6 g of lithium chloride, 55 ml of 2 molar sodium carbonate solution and 7.2 g (46.8 mmol) of 4-methoxyphenylboronic acid are added thereto in succession. The reaction mixture is then stirred at 95° C. for 2 hours and cooled to room temperature, and saturated sodium chloride solution is added. The organic phase is removed and washed in succession with 50 % sodium hydroxide solution and water, dried over sodium sulphate and concentrated in vacuo. The residue is chromatographed on silica gel with a mixture of ethyl acetate/hexane. 19.2 g of 3,3;17,17-bis-(ethylenedioxy)-11-(4-methoxyphenyl)-5,9(11)-oestradiene are obtained in the form of a white foam.

c) 3,3;17,17-Bis-(ethylenedioxy)-11β-(4-methoxyphenyl)-5-oestrene 800 ml of ammonia are condensed at −70° C. and 1.39 g of lithium are added. After the characteristic blue colouring appears, 18.6 g (40 mmol) of 3,3;17,17-bis-(ethylenedioxy)-11-(4-methoxyphenyl)-5,9(11)-oestradiene dissolved in 400 ml of tetrahydrofuran are added dropwise. After stirring the mixture for 20 minutes, the excess lithium is decomposed by the addition of water, and the ammonia is evaporated off. The reaction mixture is poured onto saturated ammonium chloride solution and the aqueous phase is extracted with ethyl acetate. The combined organic phases are washed with saturated sodium chloride solution, dried over sodium sulphate and concentrated in vacuo. After chromatography of the crude product on silica gel with a mixture of ethyl acetate/hexane, 15.2 g of 3,3;17,17-bis-(ethylenedioxy)-11β-(4-methoxyphenyl)-5-oestrene and 1.4 g of 17,17-bis-(ethylenedioxy)-11-(4-hydroxyphenyl)-5, 9(11)-oestradiene, m.p. 168°–170° C. (ethyl acetate), $[\alpha]_D^{20}$=−11° (CHCl$_3$; c=0.505), are isolated in the form of white foams.

By way of example, the preparation of some other compounds analogously to the above directions is detailed in the following Table:

| Product | Yield [%] | Physical data |
| --- | --- | --- |
| 3,3;17,17-bis-(ethylenedioxy)-11β-(4-methoxyphenyl)-5-oestrene | 81 | M.p. = 187–188° C. (diisopropyl ether); $[\alpha]_D^{20} = +2°$ (CHCl$_3$; c = 0.51) |
| 3,3;17,17-bis-(ethylenedioxy)-11β-(4-methylphenyl)-5-oestrene | 89 | M.p. = 200–201° C. (diisopropyl ether); $[\alpha]_D^{20} = +10°$ (CHCl$_3$; c = 0.375) |
| 3,3;17,17-bis-(ethylenedioxy)-11β-[4-(2-propenyl)-phenyl]-5-oestrene | 85 | $^1$H-NMR(CDCl$_3$) δ [ppm]: 7.25(2H,d J=9.5Hz, H-aromatic); 7.04(2H, d J=9.5 Hz, H-aromatic); 5.9–6.07(1H, m, H—CH=); 5.53(1H, d J=5Hz broad); 5.0–5.1(2H, m, H—CH$_2$=); 3.42(1H, tr J=5.5Hz broad, H-11); 3.34(2H, d J=6Hz, H—CH$_2$-ar); 0.56 (3H, s, H-18) | d) 11β-(4-Methoxyphenyl)-4-oestrene-3,17-dione 19.2 g of 3,3;17,17-bis-(ethylenedioxy)-11β-(4-methoxyphenyl)-5-oestrene are dissolved in 500 ml of acetone and, under an inert gas, 12.5 ml of 4N aqueous hydrochloric acid are added. The reaction mixture is stirred for 2 hours at 40° C. and then poured onto cold saturated sodium hydrogen carbonate solution, and the aqueous phase is extracted repeatedly with methylene chloride. The combined organic phases are dried over sodium sulphate and concentrated in vacuo. The residue is chromatographed on silica gel with a mixture of ethyl acetate/hexane. 12.94 g of 11β-(4-methoxyphenyl)-4-oestrene-3,17-dione are obtained in the form of a white foam.

M.p.=155°–156° C. (diisopropyl ether);
$[\alpha]_D^{20}=+169°$ (CHCl$_3$; c=0.505)

e) 3-Ethoxy-11β-(4-methoxyphenyl)-3,5-oestradien-17-one 10 g of 11β-(4-methoxyphenyl)-4-oestrene-3,17-dione are placed in a mixture of 260 ml of absolute methylene chloride, 29 ml of ethanol and 26.4 ml of orthoformic acid triethyl ester and, at 0° C., 100 mg of p-toluenesulphonic acid (monohydrate) are added. The whole is then stirred for 3.5 hours at ice-bath temperature and then an excess of saturated sodium hydrogen carbonate solution is added to the reaction mixture. The aqueous phase is extracted repeatedly with methylene chloride and the combined organic phases are dried over sodium sulphate and concentrated in vacuo. The crude product is used directly in the subsequent reaction step. 10.8 g of crude 3-ethoxy-11β-(4-methoxyphenyl)-3,5-oestradien-17-one are isolated.

f) 3-Ethoxy-11β-(4-methoxyphenyl)-17α-(prop-1-ynyl)-3,5-oestradien-17-ol 1.2 l of absolute tetrahydrofuran are saturated with propyne at 0° C. 165 ml of a 1.6M n-butyllithium solution (hexane) are then slowly added dropwise to that solution without a great increase in temperature. After the reaction mixture has subsequently been stirred for 15 minutes, a solution of the ketone prepared in e) (10.8 g), dissolved in 130 ml of absolute tetrahydrofuran, is slowly added dropwise while cooling with an ice-bath, and the mixture is then stirred for 60 minutes and subsequently poured onto water. The aqueous phase is extracted with ethyl acetate and the organic phase is washed with sodium chloride solution. After drying over sodium sulphate and concentrating the organic phase in vacuo, the residue (11.8 g) is directly further reacted as described in the following.

g) 6β-Bromo-17β-hydroxy-11β-(4-methoxyphenyl)-17α-(prop-1-ynyl)-4-oestren-3-one 11.8 g of the crude product prepared in f) are suspended in a mixture of 120 ml of 80% aqueous dioxan solution and 56 ml of 10% aqueous sodium acetate solution. 3.8 g of 1,3-dibromo-5,5-dimethylhydantoin are added in portions at 0° C. to that suspension. The steroid slowly dissolves during the course of the addition. After a reaction time of 30 minutes, the reaction mixture is poured onto water and the aqueous phase is extracted with methylene chloride. The combined organic phases are washed with saturated sodium thiosulphate solution and water, dried over sodium sulphate and concentrated in vacuo. 13.4 g of crude 6β-bromo-17β-hydroxy-11β-(4-methoxyphenyl)-17α-(prop-1-ynyl)-4-oestren-3-one is obtained, which is used directly in the next reaction step.

h) 17β-Hydroxy-11β-(4-methoxyphenyl)-17α-(prop-1-ynyl)-4,6-oestradien-3-one 13.4 g of the bromine compound prepared in g) are dissolved in 115 ml of absolute dimethylformamide, 3.9 g of lithium carbonate and 5.75 g of lithium bromide are added under inert gas, and the whole is stirred for one hour at 100° C. The reaction mixture is cooled to room temperature and then poured onto water, the aqueous phase is neutralised with 4N hydrochloric acid and the aqueous phase is extracted repeatedly with ethyl acetate. The combined organic phases are washed repeatedly with saturated sodium chloride solution, dried over sodium sulphate and concentrated in vacuo. The residue is chromatographed on silica gel with a mixture of ethyl acetate/hexane. 5.6 g of the title compound are isolated in the form of a yellowish foam.

$^1$H-NMR (CDCl$_3$) δ [ppm]: 7.32 (2H, d J=9 Hz, H-aromatic); 6.83 (2H, d J=9Hz, H-aromatic); 6.21–6.73 (2H, m, H-6 and H-7); 5.8 (1H, s, H-4); 3.8 (3H, s, H-methyl ether); 3.4 (1H, tr broad J=6 Hz, H-11); 1.88 (3H, s, H-propyne); 0.63 (3H, s, H-18).

EXAMPLE 2

17β-Hydroxy-11β-(4-methoxyphenyl)-7β-methyl-17α-(prop-1-ynyl)-4-oestren-3-one and

EXAMPLE 3

17β-Hydroxy-11β-(4-methoxyphenyl)-7α-methyl-17α-(prop-1-ynyl)-4-oestren-3-one 78 ml of a 1.6M solution of methyllithium in diethyl ether are placed in 120 ml of ether at 0° C., 11.8 g of copper(I) iodide are added and the whole is then stirred for one hour. There is then added dropwise to the dimethyl cuprate a solution of 2.5 g of the dienone prepared in Example 1H) in 30 ml of absolute tetrahydrofuran. After a reaction time of one hour, the mixture is poured into dilute aqueous ammonia solution and the aqueous phase is extracted repeatedly with ethyl acetate. The combined organic phases are washed with saturated sodium chloride solution, dried over sodium sulphate and concentrated in vacuo to yield the crude product. The crude product is taken up in 60 ml of acetone, 3 ml of 4N aqueous hydrochloric acid are added and the whole is stirred at room temperature for one hour. The reaction mixture is then poured onto saturated sodium hydrogen carbonate solution and the aqueous phase is extracted repeatedly with ethyl acetate. The combined organic phases are washed with saturated sodium chloride solution, dried over sodium sulphate and concentrated in vacuo. The residue is chromatographed on silica gel with a mixture of ethyl acetate/hexane and 1.35 g of a mixture of the title compounds are isolated in the form of a white foam. Separation by HPLC on Hypersil (ODS=octadecylsilane, 5µ) with a mixture of water and acetonitrile yields 773 mg of 17β-hydroxy-11β-(4-methoxyphenyl)-7α-methyl-17α-(prop-1-ynyl)-4-oestren-3-one and 235 mg of 17β-hydroxy-11β-(4-methoxyphenyl)-7β-methyl-17α-(prop-1-ynyl)-4-oestren-3-one in the form of white foams.

Compound 2

$^1$H-NMR (CDCl$_3$) δ [ppm]: 7.34 (2H, d J=9 Hz, H-aromatic); 6.83 (2H, d J=9 Hz, H-aromatic); 5.83 (1H, s, H-4); 3.8 (3H, s, H-methyl ether); 3.4 (1H, tr broad J=5.5 Hz, H-11); 1.89 (3H, s, H-propyne); 1.17 (3H, d J=6 Hz, H-7-methyl group); 0.59 (3H, s, H-18).

Compound 3

$^1$H-NMR (CDCl$_3$) δ [ppm]: 7.32 (2H, d J=9 Hz, H-aromatic); 6.82 (2H, d J=9 Hz, H-aromatic); 5.87 (1H, s, H-4); 3.8 (3H, s, H-methyl ether); 3.4 (1H, tr broad J=5.5 Hz, H-11); 1.89 (3H, s, H-propyne); 0.87 (3H, d J=7.5 Hz, H-7-methyl group); 0.65 (3H, s, H-18).

EXAMPLE 4

11β-(4-Acetylphenyl)-17β-hydroxy-17α-(3-hydroxyprop-1(Z)-enyl)-6β-methyl-4-oestrane a) 3,3;17,17-Bis-(ethylenedioxy)-11β-(4-methoxyphenyl)-5α, 6α-epoxy-oestrane 20 g of the diketal prepared in Example 1 c) are dissolved in 200 ml of methylene chloride. 0.1 ml of pyridine are added, the whole is cooled to 0° C., and 0.9 ml of hexachloroacetone is added. 9.2 ml of a 30% aqueous hydrogen peroxide solution are then added dropwise. The whole is stirred at room temperature for 7 days and then saturated sodium thiosulphate solution is cautiously added to the reaction solution with gentle cooling. The aqueous phase is removed and extracted repeatedly with methylene chloride and the organic phases are combined, washed with saturated sodium chloride solution, dried over sodium sulphate and concentrated in vacuo. The crude product is purified by chromatography on silica gel with a mixture of ethyl acetate and hexane. 16.6 g of 3,3;17,17-bis-(ethylenedioxy)-11β-(4-methoxyphenyl)-5α,6α-epoxy-oestrane are obtained in the form of a white foam.

M.p.=239°–241° C. (ethyl acetate);
$[α]_D^{20}$=−44° (CHCl$_3$; c=0.505)

b) 3,3;17,17-Bis-(ethylenedioxy)-11β-(4-methoxyphenyl)-6β-methyl-oestran-5α-ol

Under inert gas, 15 g of the epoxide prepared in a) are dissolved in 200 ml of absolute tetrahydrofuran, 138 ml of a 3M methylmagnesium chloride solution (tetrahydrofuran) are added and then the mixture is stirred for 22 hours at room temperature. The reaction mixture is subsequently poured onto saturated ammonium chloride solution and the aqueous phase is extracted with ethyl acetate. The combined organic phases are washed with saturated sodium chloride solution, dried over sodium sulphate and concentrated in vacuo. The crude product is purified by chromatography on silica gel with a mixture of ethyl acetate and hexane. 13.8 g of 3,3;17,17-bis-(ethylenedioxy)-11β-(4-methoxyphenyl)-6β-methyl-oestran-5α-ol are obtained in the form of a white foam.

M.p.=168°–169° C. (ethyl acetate);
$[α]_D^{20}$=−36° (CHCl$_3$; c=0.505)

c) 3,3;17,17-Bis-(ethylenedioxy)-11β-(4-hydroxyphenyl)-6β-methyl-oestran-5α-ol 13 g of the anisole prepared in b) are dissolved in 130 ml of absolute dimethylformamide, 7.3 g of sodium methanethiolate are added and the reaction mixture is heated under reflux for 1.5 hours. The whole is cooled and poured onto water and the aqueous phase is extracted with ethyl acetate. The combined organic phases are washed repeatedly with saturated sodium chloride solution, dried over sodium sulphate and concentrated in vacuo. The residue is chromatographed on silica gel with a mixture of ethyl acetate/hexane and 8.95 g of 3,3;17,17-bis-(ethylenedioxy)-11β-(4-hydroxyphenyl)-6β-methyl-oestran-5α-ol are obtained in the form of a white foam.

d) 3,3;17,17-Bis-(ethylenedioxy)-6β-methyl-11β-(4-trifluoromethylsulphonyloxyphenyl)-oestran-5α-ol Under inert gas, 8.5 g of the phenol prepared in c) are dissolved, together with 11.75 g of 4-dimethylaminopyridine, in 175 ml of absolute methylene chloride, the solution is cooled to −78° C. and 3.85 ml of trifluoromethanesulphonic acid anhydride, dissolved in 23 ml of absolute methylene chloride, are added. The reaction mixture is then stirred for 1.5 hours and subsequently poured onto saturated sodium hydrogen carbonate solution, and the aqueous phase is extracted repeatedly with methylene chloride. The combined organic phases are washed with saturated sodium chloride solution, dried over sodium sulphate and concentrated in vacuo. The residue is chromatographed on silica gel with a mixture of ethyl acetate/hexane to yield 7.76 g of 3,3;17,17-bis-(ethylenedioxy)-6β-methyl-11β-(4-trifluoromethylsulphonyloxyphenyl)-oestran-5α-ol in the form of a white foam.

$[α]_D^{20}$=−28° (CHCl$_3$; c=0.505)

e) 3,3-(Ethylenedioxy)-5α-hydroxy-6β-methyl-11β-(4-trifluoromethylsulphonyloxyphenyl)-oestran-17-one 19 g of silica gel are suspended in 38 ml of methylene chloride, 194 ml of saturated oxalic acid solution are added and the whole is then stirred for 15 minutes. 7.7 g of the triflate prepared in d) are added to that suspension, and the reaction mixture is then stirred at room temperature for 2.5 hours. The mixture is subsequently suction-filtered through a frit, the frit residue is washed with methanol/methylene chloride, and the filtrate so-obtained is extracted by shaking with saturated sodium hydrogen carbonate solution. The organic phase is dried over sodium sulphate and concentrated in vacuo. The residue is chromatographed on silica gel with a mixture of ethyl acetate/hexane. 4.08 g of 3,3-(ethylenedioxy)-5α-hydroxy-6β-methyl-11β-(4-trifluoromethylsulphonyloxyphenyl)-oestran-17-one are obtained in the form of a white foam.

$[α]_D^{20}$ =42° (CHCl$_3$; c=0.53)

f) 11β-[4-(1-Ethoxyvinyl)phenyl]-3,3-(ethylenedioxy)-5α-hydroxy-6β-methyloestran-17-one 4 g of the triflate prepared in e) are dissolved in 35 ml of absolute dioxan and 585 mg of lithium chloride and 0.8 g of tetrakistriphenylphosphinepalladium are added. The reaction mixture is stirred for 5 minutes and then 2.91 ml of tri-n-butyl-(1-ethoxyvinyl)-tin are added. The whole is stirred at reflux for 1 hour under an inert gas, cooled to room temperature and diluted with ethyl acetate. After filtration through Celite and washing the filtration residue with ethyl acetate, the organic phase is washed with saturated sodium chloride solution, dried over sodium sulphate and concentrated in vacuo. The crude product is used directly in the next reaction step.

g) -11β-[4-(1-Ethoxyvinyl)-phenyl]-3,3-(ethylenedioxy)-17α-(3-hydroxyprop-1-ynyl)-6β-methyl-oestrane-5α,17β-diol The crude product obtained in f) is dissolved in 100 ml of absolute tetrahydrofuran and, at 0° C., 16 g of potassium ethoxide and 5.6 ml of propargyl alcohol are added in succession. The reaction mixture is stirred for one hour at 0° C. and for three hours at room temperature and then poured onto saturated ammonium chloride solution.

The aqueous phase is extracted with ethyl acetate and the combined organic phases are washed with saturated sodium chloride solution, dried over sodium sulphate and concentrated in vacuo. The crude product is purified by chromatography on silica gel with a mixture of ethyl acetate and hexane. 1.96 g of 11β-[4-(1-ethoxyvinyl)-phenyl]-3,3-(ethylenedioxy)-17α-(3-hydroxyprop-1-ynyl)-6β-methyl-oestrane-5α,17β-diol are obtained in the form of a white foam.

h) -11β-(4-Acetylphenyl)-5α,17β-dihydroxy-17α-(3-hydroxy-prop-1-ynyl)-6β-methyl-oestran-3-one 1.9 g of the diol prepared in g) are dissolved in 95 ml of acetone and 9.5 ml of 4N aqueous hydrochloric acid are added under inert gas. The reaction mixture is stirred for 2 hours at 0° C. and then poured onto cold saturated sodium hydrogen carbonate solution and the aqueous phase is extracted repeatedly with methylene chloride. The combined organic phases are dried over sodium sulphate and concentrated in vacuo. The residue is chromatographed on silica gel with a mixture of ethyl acetate/hexane. 1.42 g of 11β-(4-acetylphenyl)-5α,17β-dihydroxy-17α-(3-hydroxyprop-1-ynyl)-6β-methyl-oestran-3-one are obtained in the form of a white foam.

i) 11β-(4-Acetylphenyl)-5α,17β-dihydroxy-17α-(3-hydroxy-prop-1(Z)-enyl)-6β-methyl-oestran-3-one 1.3 g of the acetylene prepared in h) are dissolved in 13 ml of tetrahydrofuran, 1.3 ml of pyridine are added, and the whole is hydrogenated at normal pressure using 130 mg of palladium (10%) on barium sulphate as catlyst. When one equivalent of hydrogen has been taken up, the reaction mixture is filtered through Celite, the filtration residue is washed with ethyl acetate and the filtrate is concentrated in vacuo. The residue is chromatographed on silica gel with a mixture of hexane/ethyl acetate and 1.12 g of 11β-(4-acetylphenyl)-5α,17β-dihydroxy-17α-(3-hydroxyprop-1(Z)-enyl)-6β-methyl-oestran-3-one are obtained in the form of a white foam.

j) -11β-(4-Acetylphenyl)-17β-hydroxy-17α-(3-hydroxyprop-1(Z)-enyl)-6β-methyl-4-oestren-3-one 1.1 g of the ketone prepared in i) are dissolved in 45 ml of ethanol under inert gas and 2.2 ml of 0.1N aqueous sodium hydroxide solution are added. The reaction mixture is stirred for 6 hours, then water is added and the mixture is neutralised with 4N aqueous hydrochloric acid. The aqueous phase is extracted repeatedly with ethyl acetate and the combined organic phases are washed with saturated sodium chloride solution, dried over sodium sulphate and concentrated in vacuo. The residue is chromatographed on silica gel with a mixture of ethyl acetate/hexane. 875 mg of the title compound are obtained in the form of a white foam.

$^1$H-NMR (CDCl$_3$) δ [ppm]: 7.91 (2H, d J=9 Hz, H-aromatic); 7.3 (2H, d J=9Hz, H-aromatic); 5.9 (1H, d J=1 Hz, H-4); 5.59–5.8 (2H, m, H-20 and H-21); 4.26 (2H, d J=5.5 Hz, H-22); 3.42 (1H, tr broad J=5.5 Hz, H-11); 2.6 (3H, s, H-acyl group); 1.36 (3H, d J=7Hz, H-6-methyl group); 0.68 (3H, s, H-18).

EXAMPLE 5

17β-Hydroxy-11β-(4-acetylphenyl)-17α-(3-Hydroxyprop-1 (Z)-enyl)-6α-methyl-4-oestren-3-one 600 mg of the -11β-(4-acetylphenyl)-17β-hydroxy-17α-(3-hydroxyprop-1(Z)-enyl)-6β-methyl-4-oestren-3-one prepared in Example 4 j) are treated with 4N aqueous hydrochloric acid in acetone analogously to the directions given in Example 1 d). After working up, the crude product is purified by HPLC on Hypersil (ODS 5μ) with a mixture of water and methanol. 385 mg of the title compound are isolated in the form of a white foam.

$^1$H-NMR (CDCl$_3$) δ [ppm]: 7.87 (2H, d J=9Hz, H-aromatic); 7.55 (2H, d J=9Hz, H-aromatic); 5.87 (1H, s, H-4); 5.55–5.75 (2H, m, H-20and H-21); 4.26 (2H, d J=5.5Hz, H-22); 3.42 (1H, dd broad J$_1$=5.5 and J$_2$=11Hz, H-11); 2.58 (3H, s, H-acyl group); 1.15 (3H, d J=5.5Hz, H-6-methyl group); 0.65 (3H, s, H-18).

EXAMPLE 6

17β-Hydroxy-17α-(3-Hydroxyprop-1-ynynl)-6β-methyl-11β-[4-(3-pyridyl)-phenyl1]-4-oestren-3-one a) 3,3-(Ethylenedioxy)-5α-hydroxy-6β-methyl-11β-[4-(3-pyridyl)-phenyl]-oestran-17-one 10 g of the 3,3-(ethylenedioxy)-5α-hydroxy-6β-methyl-11β-(4-trifluoromethylsulphonyloxyphenyl)-oestran-17-one prepared in accordance with the directions given in Example 4 e) are dissolved in a mixture of 80 ml of toluene and 35 ml of ethanol and 1 g of palladium tetrakistriphenylphosphine, 1.47 g of lithium chloride, 22.5 ml of 2M sodium carbonate solution and 2.8 g of diethyl-(3-pyridyl)-borane are added in succession. The reaction mixture is then stirred at 110° C. for 3 hours and cooled to room temperature, and saturated sodium chloride solution is added. The organic phase is removed, washed in succession with 5% sodium hydroxide solution and water, dried over sodium sulphate and concentrated in vacuo. The residue is chromatographed on silica gel with a mixture of ethyl acetate/hexane. 7.53 g of 3,3-(ethylenedioxy)-5α-hydroxy-6β-methyl-11β-[4-(3-pyridyl)-phenyl]-oestran-17-one are obtained in the form of a white foam.

$[α]_D^{20}$=58° (CHCl$_3$; c=0.52)

b) 3,3-(Ethylenedioxy)-17α-(3-hydroxyprop-1-ynyl)-6β-methyl-11β-[4-(3-pyridyl)-phenyl]-oestrane-5α,17β-diol 7 g of the ketone prepared in a) are reacted with potassium ethoxide and propargyl alcohol analogously to the directions given in Example 4 g) to yield 5.83 g of 3,3-(ethylenedioxy)-17α-(3-hydroxyprop-1-ynyl)-6β-methyl-11β-[4-(3-pyridyl)-phenyl]-oestrane-5α,17β-diol, which is isolated in the form of a white foam.

c) 5α,17β-Dihydroxy-17α-(3-hydroxyprop-1-ynyl)-6β-methyl-11β-[4-(3-pyridyl)-phenyl]-oestran-3-one 5 g of the triol prepared in b) are reacted with 4N aqueous hydrochloric acid in acetone at 0° C. analogously to the directions given in Example 4 h) to yield 4.02 g of 5α,17β-dihydroxy-17α-(3-hydroxyprop-1-ynyl)-6β-methyl-11β-[4-(3-pyridyl)-phenyl]-oestran-3-one, which is isolated in the form of a white foam.

$[α]_D^{20}$=−62° (CHCl$_3$; c=0.505)

d) 17β-Hydroxy-17α-(3-hydroxyprop-1-ynyl)-6β-methyl--11β-[4-(3-pyridyl)-phenyl]-4-oestren-3-one 1.75 g of the ketone prepared in c) are reacted with 2N aqueous sodium hydroxide solution in ethanol analogously to the directions given in Example 4 j). 1.45 g of the title compound are isolated in the form of a white foam.

¹H-NMR (CDCl₃) δ [ppm]: 8.87 (1H, s broad, H-heteroaromatic); 8.59 (1H, d J=5Hz, H-heteroaromatic); 7.9 (1H, dtr $J_1$=1.5 and $J_2$=9Hz, H-heteroaromatic); 7.48–7.63 (4H, m, H-aromatic); 7.38 (1H, dd $J_1$=5 and $J_2$=9Hz, H-heteroaromatic); 5.91 (1H, d J=1Hz, H-4); 5.36 (2H, s, H-22); 3.46 (1H, tr broad J=5.5Hz, H-11); 1.38 (3H, d J=6.5Hz, H-6-methyl group); 0.7 (3H, s, H-18).

EXAMPLE 7

17β-Hydroxy-17α-(3-hydroxyprop-1(Z)-enyl)-6β-methyl-11β-[4-(3-pyridyl)-phenyl]-4-oestren-3-one a) 5α,17β-Dihydroxy-17α-(3-hydroxyprop-1(Z)-enyl)-6β-methyl-11β-[4-(3-pyridyl)-phenyl]-oestran-3-one 2 g of the ketone prepared in 6 c) are hydrogenated analogously to the directions given in Example 4 i). 1.68 g of 5α,17β-dihydroxy-17α-(3-hydroxyprop-1(Z)-enyl)-6β-methyl-11β-[4-(3-pyridyl)-phenyl]-oestran-3-one are isolated in the form of a white foam.

b) 17β-Hydroxy-17α-(3-hydroxyprop-1(Z)-enyl)-6β-methyl-11β-[4-(3-pyridyl)-phenyl]-4-oestren-3-one 1.5 g of the ketone prepared in a) are reacted with 2N aqueous sodium hydroxide solution in ethanol analogously to the directions given in Example 4 j). 1.15 g of the title compound are isolated in the form of a white foam.

$[α]_D^{20}$=62° (CHCl₃; c=0.5)

¹H-NMR (CDCl₃) δ [ppm]: 8.88 (1H, s broad, H-heteroaromatic); 8.59 (1H, d J=5Hz, H-heteroaromatic); 7.9 (1H, dtr $J_1$=1.5 and $J_2$=9Hz, H-heteroaromatic); 7.49–7.57 (4H, m, H-aromatic); 7.39 (1H, dd $J_1$=5 and $J_2$=9Hz, H-heteroaromatic); 5.9 (1H, d J=1Hz, H-4); 5.6–5.8 (2H, m, H-20 and H-21); 5.27 (2H, d J=6Hz, H-22); 3.42 (1H, tr broad J=5.5Hz, H-11); 1.35 (3H, d J=6.5Hz, H-6-methyl group); 0.75 (3H, s, H-18).

EXAMPLE 8

17β-Hydroxy-17α-(3-hydroxyprop-1(Z)-enyl)-6α-methyl-11β-[4-(3-pyridyl)-phenyl]-4-oestren-3-one 800 mg of the 17β-hydroxy-17α-(3-hydroxyprop-1(Z)-enyl)-6β-methyl-11β-[4-(3-pyridyl)-phenyl]-4-oestren-3-one prepared in Example 7 b) are treated with 4N aqueous hydrochloric acid in acetone analogously to the directions given in Example 1 d). After working up, the crude product is purified by HPLC on Hypersil (ODS 5µ) with a mixture of water and acetonitrile. 463 mg of the title compound are isolated in the form of a white foam.

$[α]_D^{20}$=80° (CHCl₃; c=0.505)

¹H-NMR (CDCl₃) δ [ppm]: 8.85 (1H, s broad, H-heteroaromatic); 8.57 (1H, d J=5Hz, H-heteroaromatic); 7.9 (1H, dtr $J_1$=1.5 and $J_2$=9Hz, H-heteroaromatic); 7.45–7.57 (4H, m, H-aromatic); 7.38 (1H, dd $J_1$=5 and $J_2$=9Hz, H-heteroaromatic); 5.88 (1H, s, H-4); 5.6–5.8 (2H, m, H-20 and H-21); 5.28 (2H, d J=5Hz, H-22); 3.42 (1H, tr broad J=5.5Hz, H-11); 1.16 (3H, d J=5.5Hz, H-6-methyl group); 0.73 (3H, s, H-18).

EXAMPLE 9

11β-(4-Dimethylaminophenyl)-17β-hydroxy-17α-(prop-1-ynyl)-4,6-oestradien-3-one a) 11β-(4-Dimethylaminophenyl)-4-oestren-3,17-dione 6.6 g of the title compound are obtained as crude product from 10 g of 3,3;17,17-bis-(ethylenedioxy)-11β-(4-dimethylaminophenyl)-5-oestrene (for preparation see EP-A 50343) analogously to the directions given in Example 1 d).

¹H-NMR (CDCl₃) δ [ppm]: 7.27 (2H, d J=9Hz, H-aromatic); 6.67 (2H, d J=9Hz, H-aromatic); 5.88 (1H, s, H-4); 3.32 (1H, tr broad J=5.5Hz, H-11); 2.94 (6H, s, H—NMe2); 0.70 (3H, s, H-18).

b) -11β-(4-Dimethylaminophenyl)-3-ethoxy-3,5-oestradien-17-one 4.04 g of the title compound are obtained as crude product from 3.75 g of 11β-(4-dimethylaminophenyl)-4-oestren-3,17-dione analogously to the directions given in Example 1 e).

c) -11β-(4-Dimethylaminophenyl)-3-ethoxy-17α-(prop-1-ynyl)-3,5-oestradien-17β-ol 1.98 g of the title compound are obtained in the form of a white foam from 4.04 g of 11β-(4-dimethylaminophenyl)-3-ethoxy-3,5-oestradien-17-one analogously to the directions given in Example 1 f).

d) 6β-Bromo-11β-(4-dimethylaminophenyl)-17β-hydroxy-17α-(prop-1-ynyl)-4-oestren-3-one and 6β-bromo-11β-(3-bromo-4-dimethylaminophenyl)-17β-hydroxy-17α-(prop-1-ynyl)-4-oestren-3-one Analogously to the directions given in Example 1 g), 1.09 g and 635 mg of the title compounds are obtained in the form of yellowish foams from 1.9 g of 11β-(4-dimethylaminophenyl)-3-ethoxy-17α-(prop-1-ynyl)-3,5-oestradien-17β-ol with 0.613 equivalents of 1,3-dibromo-5,5-dimethylhydantoin.

e) 11β-(4-Dimethylaminophenyl)-17β-hydroxy-17α-(prop-1-ynyl)-4,6-oestradien-3-one 465 mg of the title compound are obtained in the form of a yellowish foam from 0.9 g of 6β-bromo-11β-(4-dimethylaminophenyl)-17β-hydroxy-17α-(prop-1-ynyl)-4-oestren-3-one analogously to the directions given in Example 1 h).

¹H-NMR (CDCl₃) δ [ppm]: 7.25 (2H, d J=9Hz, H-aromatic); 6.67 (2H, d J=9Hz, H-aromatic); 6.2–6.33 (2H, m, H-6 and H-7); 5.8 (1H, s, H-4); 3.36 (1H, tr broad J=6Hz, H-11); 2.95 (6H, s, H-methyl groups at the nitrogen); 1.88 (3H, s, H-propyne); 0.67 (3H, s, H-18).

$[α]_D^{20}$=−23° (CHCl₃; c=0.505)

EXAMPLE 10

11β-(3-Bromo-4-dimethylaminophenyl)-17β-hydroxy-17α-(prop-1-ynyl)-4,6-oestradien-3-one 235 mg of the title compound are obtained in the form of a yellowish foam from 0.55 g of 6β-bromo-11β-(3-bromo-4-dimethylaminophenyl)-17β-hydroxy-17α-(prop-1-ynyl)-4-oestren-3-one analogously to the directions given in Example 1 h).

¹H-NMR (CDCl₃) δ [ppm]: 7.53 (1H, d J=1Hz, H-aromatic); 7.31 (1H, dd J=1Hz and $J_1$=9Hz, H-aromatic); 6.98 (1H, d $J_1$=9Hz, H-aromatic); 6.21–6.34 (2H, m, H-6 and H-7); 5.81 (1H, s, H-4); 3.36 (1H, tr broad J=6Hz, H-11); 2.8 (6H, s, H-methyl groups at the nitrogen); 1.88 (3H, s, H-propyne); 0.63 (3H, s, H-18).

$[α]_D^{20}$=−30° (CHCl₃; c=0.515)

EXAMPLE 11

11β-(4-Acetylphenyl)-17β-hydroxy-17α-(prop-1-ynyl)-4,6-oestradien-3-one.

a) 3,3;17,17-Bis-(ethylenedioxy)-11β-(4-hydroxyphenyl)-5-oestrene 130 g of the compound prepared in Example 1 c) are dissolved in 1.4 l of absolute dimethylformamide, 7.81 g of sodium methanethiolate are added and the reaction mixture is heated under reflux for 3 hours. The mixture is cooled and then poured onto water and the aqueous phase is extracted with ethyl acetate. The combined organic phases are washed repeatedly with saturated sodium chloride solution, dried over sodium sulphate and concentrated in vacuo. The residue is chromatographed on silica gel with a mixture of ethyl acetate/hexane and 76.9 g of 3,3;17,17-Bis-(ethylenedioxy)-11β-(4-hydroxyphenyl)-5-oestrene are obtained in the form of a white foam.

M.p.=224°–225° C. (diisopropyl ether);
$[\alpha]_D^{20}$=+1.5° (CHCl$_3$; c=0.505)

b) 3,3;17,17-Bis-(ethylenedioxy)-11β-(4-trifluoromethyl-sulphonyloxyphenyl)-5-oestrene 73.5 g of the title compound are obtained in the form of a white foam from 76.1 g of 3,3;17,17-bis-(ethylene-dioxy)-11β-(4-hydroxyphenyl)-5-oestrene analogously to the directions given in Example 4 d).

c) -11β-(4-Trifluoromethylsulphonyloxyphenyl)-4-oestrene-3,17-dione 51.3 g of the title compound are obtained in the form of a crystallisate from 73 g of 3,3;17,17-bis-(ethylene-dioxy)-11β-(4-trifluoromethylsulphonyloxyphenyl)-5-oestrene analogously to the directions given in Example 1 d).

d) 3-Ethoxy-11β-(4-trifluoromethylsulphonyloxyphenyl)-3,5-oestradien-17-one 53.5 g of the title compound are obtained as crude product from 50 g of -11β-(4-trifluoromethylsulphonyloxy-phenyl)-4-oestren-3,17-dione analogously to the directions given in Example 1 e).

e) 3-Ethoxy-17α-(prop-1-ynyl)-11β-(4-trifluoromethyl-sulphonyloxyphenyl)-3,5-oestradien-17β-ol 34.1 g of the title compound are obtained as crude product from 31.7 g of 3-ethoxy-11β-(4-trifluoromethyl-sulphonyloxyphenyl)-3,5-oestradien-17-one analogously to the directions given in Example 1 f).

f) 6β-Bromo-17β-hydroxy-17α-(prop-1-ynyl)-11β-(4-trifluoromethylsulphonyloxyphenyl)-4oestren-3-one 17.2 g of the title compound are obtained in the form of a white foam from 34.1 g of 3-ethoxy-17α-(prop-1-ynyl)-11β-(4-trifluoromethylsulphonyloxyphenyl)-3,5-oestradien-17β-ol analogously to the directions given in Example 1 g).

M.p. 166° C. (diisopropyl ether)
$[\alpha]_D^{20}$=−73° (CHCl$_3$; c=0.505)

g) 17β-Hydroxy-17α-(prop-1-ynyl)-11β-(4-trifluoromethyl-sulphonyloxyphenyl)-4,6-oestradien-3-one 9.1 g of the title compound are obtained in the form of a yellowish foam from 11.3 g of 6β-bromo-17β-hydroxy-17α-(prop-1-ynyl)-11β-(4-trifluoromethylsulphonyloxyphenyl)-4-oestren-3-one analogously to the directions given in Example 1 h).

M.p. 212 ° C. (diisopropyl ether)
$[\alpha]_D^{20}$=−46° (CHCl$_3$; c=0.5)

h) 11β-(4-Acetylphenyl)-17β-hydroxy-17α-(prop-1-ynyl)-4,6-oestradien-3-one 654 mg of the title compound are obtained in the form of a yellowish foam from 1 g of 17α-(prop-1-ynyl)-11β-(4-trifluoromethylsulphonyloxyphenyl)-4,6-oestradien-17β-ol analogously to the directions given in Example 4 f) and 4 h).

$^1$H-NMR (CDCl$_3$) δ [ppm]: 7.9 (2H, d J=9Hz, H-aromatic); 7.53 (2H, d J=9Hz, H-aromatic); 6.23–6.35 (2H, m, H-6 and H-7); 5.83 (1H, s, H-4); 3.5 (1H, tr broad J=6Hz, H-11); 2.62 (3H, s, H-methylketone); 1.88 (3H, s, H-propyne); 0.58 (3H, s, H-18).

M.p. =250 C. (decomposition) (diisopropyl ether)
$[\alpha]_D^{20}$=−5.4° (CHCl$_3$; c=0.51)

EXAMPLE 12

11β-[4-(3-Furanyl)-phenyl]-17β-hydroxy-17α-(prop-1-ynyl)-4.6-oestradien-3-one.

379 mg of the title compound are obtained in the form of a yellowish foam from 535 mg of the compound produced in Example 11 g) by coupling with 0.5 ml of 3-tri-n-butyl-stannylfuran analogously to the directions given in Example 4 f).

$^1$H-NMR (CDCl$_3$) δ [ppm]: 7.74 (1H, s broad, H-heteroaromatic); 7.49 (1H, tr J=0.5Hz, H-heteroaromatic); 7.42 (4H, s, H-aromatic); 6.7 (4H, d J=0.5Hz, H-heteroaromatic); 6.24–6.34 (2H, m, H-6 and H-7); 5.81 (1H, s, H-4); 3.45 (1H, tr broad J=6Hz, H-11); 1.89 (3H, s, H-propyne); 0.65 (3H, s, H-18).

M.p.=200° C. (diisopropyl ether)
$[\alpha]_D^{20}$=7° (CHCl$_3$; c=0.51)

EXAMPLE 13

11β-[4-(4-Cyanophenyl)-phenyl]-17β-hydroxy-17α-(prop-1-ynyl)-4,6-oestradien-3-one 471 mg of the title compound are obtained in the form of a yellowish foam from 535 mg of the compound produced in Example 11 g) by coupling with 4-cyanophenylboronic acid analogously to the directions given in Example 6 a).

$^1$H-NMR (CDCl$_3$) δ [ppm]: 7.67–7.76 (4H, m, H-aromatic); 7.52 (4H, s, H-aromatic); 6.24–6.37 (2H, m, H-6 and H-7); 5.82 (1H, s, H-4); 3.5 (1H, tr broad J=6Hz, H-11); 1.88 (3H, s, H-propyne); 0.65 (3H, s, H-18).

M.p.=276° C. (decomposition) (diisopropyl ether)
$[\alpha]_D^{20}$=73° (CHCl$_3$; c=0.51)

EXAMPLE 14

17β-Hydroxy-11β-[4-(4-methylthiophenyl)-phenyl]-17α-(prop-1-ynyl)-4,6-oestradien-3-one 1.7 g of the title compound are obtained in the form of a yellowish foam from 2 g of the compound produced in Example 11 g) by coupling with 4-methylthiophenylboronic acid analogously to the directions given in Example 6a).

$^1$H-NMR (CDCl$_3$) δ [ppm]: 7.55 (2H, d J=9Hz, H-aromatic); 7.43–7.55 (4H, m, H-aromatic); 7.32 (2H, d J=9Hz, H-aromatic); 6.25–6.35 (2H, m, H-6 and H-7); 5.82 (1H, s, H-4); 3.48 (1H, tr broad J=6Hz, H-11); 2.53 (3H, s, H-methylthioether); 1.88 (3H, s, H-propyne); 0.65 (3H, s, H-18).

EXAMPLE 15

11β-[4-(4-Acetylphenyl)-phenyl]-17β-hydroxy-17α-(prop-1-ynyl)-4,6-oestradien-3-one a) 17β-Hydroxy-17α-(prop-1-ynyl)-11β-(4-tri-n-butyl-phenyl)-4,6-oestradien-3-one 12 g of the compound prepared in Example 11 g) are dissolved in 112 ml of absolute dioxan, and 1.42 g of lithium chloride and 0.7 g of tetrakistriphenylphosphine-palladium are added. After the reaction mixture has been stirred for five minutes, 16.8 ml of hexabutylditin are added, and the whole is stirred for 2.5 hours at reflux under an inert gas, cooled to room temperature and diluted with ethyl acetate. After filtration through Celite and washing the filtration residue with ethyl acetate, the organic phase is washed with saturated sodium chloride solution, dried over sodium sulphate and concentrated in vacuo. Chromatography of the residue on silica gel with a mixture of ethyl acetate/hexane yields 9.1 g of the title compound in the form of a white foam.

$^1$H-NMR (CDCl$_3$) δ [ppm]: 7.3–7.37 (4H, m, H-aromatic); 6.22–6.33 (2H, m, H-6 and H-7); 5.81 (1H, s, H-4); 3.42 (1H, tr broad J=6Hz, H-11); 1.89 (3H, s, H-propyne); 0.88 (9H, tr J=7.5Hz, H-terminal methyl groups); 0.63 (3H, s, H-18).

M.p.=154° C.

[α]$_D^{20}$=8° (CHCl$_3$; c=0.515)

b) 11β-[4-(4-Acetylphenyl)-phenyl]-17β-hydroxy-17α-(prop-1-ynyl)-4,6-ostradien-3-one 310 mg of the title compound are obtained in the form of a yellowish foam from 675 mg of 17β-hydroxy-17α-(prop-1-ynyl)-11β-(4-tri-n-butylphenyl)-4,6-oestradien-3-one analogously to the directions given in Example 4 f).

$^1$H-NMR (CDCl$_3$) δ [ppm]: 8.05 (2H, d J=9Hz, H-aromatic); 7.7 (2H, d J=9Hz, H-aromatic); 7.48–7.61 (4H, m, H-aromatic); 6.25–6.35 (2H, m, H-6 and H-7); 5.82 (1H, s, H-4); 3.49 (1H, tr broad J=6Hz, H-11); 2.65 (3H, s, H-methylketone); 1.88 (3H, s, H-propyne); 0.66 (3H, s, H-18).

EXAMPLE 16

17β-Hydroxy-17α-(prop-1-ynyl)-11β- [4-(5-pyrimidinyl)-phenyl]-4,6-oestradien-3-one 285 mg of the title compound are obtained in the form of a yellowish foam from 675 mg of 17β-hydroxy-17α-(prop-1-ynyl)-11β-(4-tri-n-butylphenyl)-4,6-oestradien-3-one analogously to the directions given in Example 4 f).

1H-NMR (CDCl$_3$) δ [ppm]: 9.2 (1H, s, H-heteroaromatic); 8.98 (2H, s, H-heteroaromatic); 7.5–7.62 (4H, m, aromatic); 6.25–6.35 (2H, m, H-6 and H-7); 5.82 (1H, s, H-4); 3.51 (1H, tr broad J=6Hz, H-11); 1.89 (3H, s, H-propyne); 0.65 (3H, s, H-18).

EXAMPLE 17

11β-[4-(3-Acetylphenyl)-phenyl]-17β-Hydroxy-17α-(prop-1-ynyl)-4.6-oestradien-3-one 301 mg of the title compound are obtained in the form of a yellowish foam from 675 mg of 17β-hydroxy-17α-(prop-1-ynyl)-11β-(4-tri-n-butylphenyl)-4,6-oestradien-3-one analogously to the directions given in Example 4 f).

$^1$H-NMR (CDCl$_3$) δ [ppm]: 8.19 (1H, tr J=0.5Hz, H-aromatic); 7.93 (1H, dtr J=0.5Hz and J$_1$=8Hz, H-aromatic); 7.8 (1H, dtr J=0.5Hz and J$_1$=8Hz, H-aromatic); 7.46–7.59 (2H, m, H-aromatic); 6.24–6.36 (2H, m, H-6 and H-7); 5.82 (1H, s, H-4); 3.5 (1H, tr broad J=6Hz, H-11); 2.67 (3H, s, H-methylketone); 1.88 (3H, s, H-propyne); 0.65 (3H, s, H-18).

EXAMPLE 18

17β-Hydroxy-17α-(3-Hydroxyprop-1-ynyl)-11β-[4-(4-methyl-thiophenyl)-phenyl]-4,6-oestradien-3-one a) 3-Ethoxy-17α-[3-(tetrahydropyran-2-yloxy)-prop-1-ynyl]-11β-(4-trifluoromethylsulphonyloxyphenyl)-3,5-oestradien-17β-ol The organolithium compound is prepared at 0° C. from 52.5 g of 3-[(tetrahydro-2H-pyran-2-yl)oxy]-1-propyne in 1300 ml of absolute tetrahydrofuran and 237 ml of a 1.6 molar solution of butyllithium in hexane. A solution of 16.5 g of the compound prepared in Example 11 d) in 300 ml of absolute tetrahydrofuran is then added dropwise. The whole is then stirred for 1 hour at 0° C., saturated ammonium chloride solution is added and the whole is extracted with ethyl acetate. The organic phase is washed with saturated sodium chloride solution, dried over sodium sulphate and concentrated in vacuo. The crude product is purified by column chromatography on silica gel with a mixture of hexane and ethyl acetate. 13.4 g of the title compound are obtained in the form of a white foam.

b) 6β-Bromo-17β-hydroxy-17α-[3-(tetrahydropyran-2-yloxy)-prop-1-ynyl]-11β-(4-trifluoromethylsulphonyloxyphenyl)-4-oestren-3-one 15.7 g of the title compound are obtained as crude product from 13 g of 3-ethoxy-17α-[3-(tetrahydropyran-2-yloxy)-prop-1-ynyl]-11β-(4-trifluoromethylsulphonyloxy-phenyl)-3,5-oestradien-17β-ol analogously to the directions given in Example 1 g).

c) 17β-Hydroxy-17α-[3-(tetrahydropyran-2-yloxy)-prop-1-ynyl]-11β-(4-trifluoromethylsulphonyloxyphenyl)-4,6-oestradien-3-one 8.7 g of the title compound are obtained in the form of a yellowish foam from 15.7 g of 6β-bromo-17β-hydroxy-17α-[3-(tetrahydropyran-2-yloxy)-prop-1-ynyl]-11β-(4-trifluoromethylsulphonyloxyphenyl)-4-oestren-3-one analogously to the directions given in example 1 h).

$^1$H-NMR (CDCl$_3$) δ [ppm]: 7.5 (2H, d J=9Hz, H-aromatic); 7.21 (2H, d J=9Hz, H-aromatic); 6.2–6.35 (2H, m, H-6 and H-7); 5.82 (1H, s, H-4); 4.83 (1H, m, H-acetal); 4.3–4.38 (2H, m, H-22); 3.8–3.91 (1H, m, H-THP-ether); 3.4–3.59 (2H, m, H-11 and H-THP-ether); 0.58 (3H, s, H-18).

d) 17β-Hydroxy-11β-[4-(4-methylthiophenyl)-phenyl]-17α-[3-(tetrahydropyran-2-yloxy)-prop-1-ynyl]-4,6-oestradien-3-one 1.05 g of the title compound are obtained in the form of a yellowish foam from 1.3 g of 17β-hydroxy-17α-[3-(tetrahydropyran-2-yloxy)-prop-1-ynyl]-11β-(4-trifluoromethylsulphonyloxyphenyl)-4,6-oestradien-3-one by coupling with 4-methylthiophenylboronic acid analogously to the directions given in Example 6 a).

e) 17β-Hydroxy-17α-(3-hydroxyprop-1-ynyl)-11β-[4-(4-methylthiophenyl)-phenyl]-4,6-oestradien-3-one 690 mg of the title compound are obtained in the form of a yellowish foam from 1 g of 17β-hydroxy-11β-[4-(4-methylthiophenyl)-phenyl]-17α-[3-(tetrahydropyran-2-yloxy)-prop-1-ynyl]-4,6-oestradien-3-one analogously to the directions given in Example 4 h).

$^1$H-NMR (CDCl$_3$) δ [ppm]: 7.42–7.57 (6H, m, H-aromatic); 7.32 (2H, d J=9Hz, H-aromatic); 6.22–6.34 (2H, m, H-6 and H-7); 5.81 (1H, s, H-4); 4.32–4.38 (2H, m, H-22); 3.48 (1H, tr broad J=6Hz, H-11); 2.52 (3H, s, H-methylthioether); 0.66 (3H, s, H-18).

EXAMPLE 19

17β-Hydroxy-17α-(3-hydroxyprop-1(Z)-enyl)-11β-[4-(4-methylthiophenyl)-phenyl]-4,6-oestradien-3-one 214 mg of the title compound are obtained in the form of a yellowish foam from 400 mg of 17β-hydroxy-17α-(3-hydroxyprop-1-ynyl)-11β-[4-(4-methylthiophenyl)-phenyl]-4,6-oestradien-3-one analogously to the directions given in Example 4 i).

$^1$H-NMR (CDCl$_3$) δ [ppm]: 7.42–7.56 (6H, m, H-aromatic); 7.32 (2H, d J=9Hz, H-aromatic); 6.22–6.33 (2H, m, H-6 and H-7); 5.6–5.88 (3H, m, H-4, H-20 and H-21); 4.23–4.32 (2H, m, H-22); 3.42 (1H, tr broad J=6Hz, H-11); 2.53 (3H, s, H-methylthioether); 0.72 (3H, s, H-18).

EXAMPLE 20

17α-Cyanomethyl-17β-Hydroxy-11β-(4-hydroxyphenyl)-4.6-oestradien-3-one a) 17α-Cyanomethyl-3-ethoxy-11β-(4-hydroxyphenyl)-3,5-oestradien-17β-ol Under inert gas, 29.9 ml of diisopropylamine are placed in 440 ml of absolute tetrahydrofuran and, at −30° C., 133 ml of a 1.6M n-butyllithium solution (hexane) are added. For complete deprotonation, the solution is then stirred at 0° C. for 30 minutes before it is cooled to −70° C. After the dropwise addition of 11.2 ml of acetonitrile, the whole is stirred for 1 hour at −70° C. 13 g (crude product) of the compound prepared in Example 11 d), dissolved in 65 ml of absolute tetrahydrofuran, are then slowly added dropwise. The reaction mixture is stirred for 60 minutes and then poured onto saturated sodium hydrogen carbonate solution, and the aqueous phase is extracted with ethyl acetate. The combined organic phases are washed with saturated sodium chloride solution, dried over sodium sulphate and concentrated in vacuo. The residue is chromatographed on silica gel with a mixture of ethyl acetate/hexane. 11.5 g of the title compound are obtained in the form of a white foam.

b) 6β-Bromo-17α-cyanomethyl-17β-hydroxy-11β-(4-hydroxyphenyl)-4-oestren-3-one 5.9 g of the title compound are obtained as crude product from 11 g of 17α-cyanomethyl-3-ethoxy-11β-(4-hydroxyphenyl)-3,5-oestradien-17β-ol analogously to the directions given in Example 1 g).

c) 17α-Cyanomethyl-17β-hydroxy-11β-(4-hydroxyphenyl)-4,6-oestradien-3-one 4.9 g of the title compound are obtained in the form of a yellowish foam from 5.7 g of 6β-bromo-17α-cyanomethyl-17β-hydroxy-11β-(4-hydroxyphenyl)-4-oestren-3-one analogously to the directions given in Example 1 h).

$^1$H-NMR (CDCl$_3$) δ [ppm]: 7.17 (2H, d J=9Hz, H-aromatic); 6.76 (2H, d J=9Hz, H-aromatic); 6.21–6.3 (2H, m, H-6 and H-7); 5.75 (1H, s, H-4); 3.34 (1H, tr broad J=6Hz, H-11); 0.67 (3H, s, H-18).

EXAMPLE 21

11β-(4-Acetylphenyl)-17α-cyanomethyl-17β-hydroxy-4,6-oestradien-3-one a) 17α-Cyanomethyl-17β-hydroxy-11β-(4-trifluoromethylsulphonyloxyphenyl)-4,6-oestradien-3-one 2.2 g of the title compound are obtained in the form of a yellowish foam from 3 g of 17α-cyanomethyl-17β-hydroxy-11β-(4-hydroxyphenyl)-4,6-oestradien-3-one analogously to the directions given in Example 4 d).

$^1$H-NMR (CDCl$_3$) δ [ppm]: 7.52 (2H, d J=9Hz, H-aromatic); 7.23 (2H, d J=9Hz, H-aromatic); 6.17–6.35 (2H, m, H-6 and H-7); 5.83 (1H, s, H-4); 3.51 (1H, tr broad J=6Hz, H-11); 2.65 (1H, d J=17.5Hz, H-20); 2.52 (1H, d J=17.5Hz, H-20); 0.65 (3H, s, H-18).

b) 11β-(4-Acetylphenyl)-17α-cyanomethyl-17β-hydroxy-4,6-oestradien-3-one 230 mg of the title compound are obtained in the form of a yellowish foam from 400 mg of 17α-cyanomethyl-17β-hydroxy-11β-(4-trifluoromethylsulphonyloxyphenyl)-4,6-oestradien-3-one analogously to the directions given in Example 4 f) and h).

$^1$H-NMR (CDCl$_3$) δ [ppm]: 7.89 (2H, d J=9Hz, H-aromatic); 7.51 (2H, d J=9Hz, H-aromatic); 6.2–6.34 (2H, m, H-6 and H-7); 5.82 (1H, s, H-4); 3.5 (1H, tr broad J=6Hz, H-11); 2.59 (3H, s, H-methylketone); 2.69 (1H, d J=17.5Hz, H-20); 2.55 (1H, d J=17.5Hz, H-20); 0.71 (3H, s, H-18).

M.p.=293° C. (decomposition) (ethyl acetate) $[α]_D^{20}$=153° (CHCl$_3$; c=0.54)

EXAMPLE 22

17α-Cyanomethyl-17β-hydroxy-11β-[4-(2-propenyl)-phenyl]-4,6-oestradien-3-one 224 mg of the title compound are obtained in the form of a yellowish foam from 400 mg of 17α-cyanomethyl-17β-hydroxy-11β-(4-trifluoromethylsulphonyloxyphenyl)-4,6-oestradien-3-one by coupling with allyltri-n-butyltin analogously to the directions given in Example 4 f).

1H-NMR (CDCl$_3$) δ [ppm]: 7.32 (2H, d J=9Hz, H-aromatic); 7.1 (2H, d J=9Hz, H-aromatic); 6.18–6.33 (2H, m, H-6 and H-7); 5.9–6.05 (1H, m, H-olefinic); 5.8 (1H, s, H-4); 5.1 (1H, tr J=0.5Hz, H-olefinic); 5.03–5.07 (1H, m, H-olefinic); 3.44 (1H, tr broad J=6Hz, H-11); 3.37 (2H, d J=7.5Hz, H-benzylic); 2.65 (1H, d J=17.5Hz, H-20); 2.5 (1H, d J=17.5Hz, H-20); 0.69 (3H, s, H-18).

M.p.=248° C. (decomposition)

$[α]_D^{20}$=92° (CHCl$_3$; c=0.52)

EXAMPLE 23

17α-Cynomethyl-17β-Hydroxy-11β-[4-(4-methylthiophenyl)-phenyl]-4.6-oestradien-3-one 356 mg of the title compound are obtained in the form of a yellowish foam from 400 mg of 17α-cyanomethyl-17β-hydroxy-11β-(4-trifluoromethylsulphonyloxyphenyl)-4,6-oestradien-3-one by coupling with 4-methylthiophenyl-boronic acid analogously to the directions given in Example 6 a).

$^1$H-NMR (CDCl$_3$) δ [ppm]: 7.43–7.57 (6H, m, H-aromatic); 7.33 (2H, d J=9Hz, H-aromatic); 6.19–6.35 (2H, m, H-6 and H-7); 5.81 (1H, s, H-4); 3.5 (1H, tr broad J=6Hz, H-11); 2.67 (1H, d J=17.5Hz, H-20); 2.53 (3H, s, H-methyl-thioether); 2.52 (1H, d J=17.5Hz, H-20); 0.71 (3H, s, H-18).

M.p.=186° C.

$[α]_D^{20}$=209° (CHCl$_3$; c=0.505)

We claim:

1. Compounds of the formula

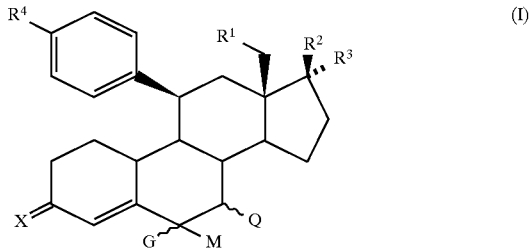

in which x represents an oxygen atom or the hydroxyimino grouping >N~OH,

R$^1$ represents a hydrogen atom or a methyl group,

R$^2$ represents a hydroxy group, a C$_1$–C$_{10}$-alkoxy group or a C$_1$–C$_{10}$-acyloxy group, R$^3$ represents a hydrogen atom; the grouping —(CH$_2$)$_n$CH$_2$Z wherein n is 0, 1, 2, 3, 4 or 5 and Z represents a hydrogen atom, a cyano group or the radical —OR$^5$ in which R$^5$=H, C$_1$–C$_{10}$-alkyl or C$_1$–C$_{10}$-alkanoyl; the grouping —(CH$_2$)$_m$C≡C—Y wherein m is 0, 1 or 2 and Y represents a hydrogen, fluorine, chlorine, bromine or iodine atom, or a C$_1$–C$_{10}$-hydroxyalkyl, C$_1$–C$_{10}$-alkoxyalkyl or C$_1$–C$_{10}$-acyloxyalkyl radical; or the grouping —(CH$_2$)$_p$—CH═CH—(CH$_2$)$_k$CH$_2$R$^6$ wherein p is 0 or 1 and k is 0, 1 or 2 and R$^6$ represents a hydrogen atom, a hydroxy group, a C$_1$–C$_4$-alkoxy radical or a C$_1$–C$_4$-acyloxy radical, or alternatively R$^2$ and R$^3$ together represent a radical of the formula

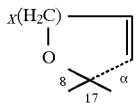

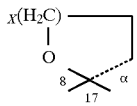

or

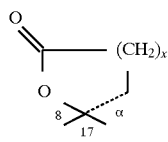

wherein x=1 or 2, $R^4$ represents a hydrogen atom; a cyano group; a chlorine, fluorine, bromine or iodine atom; a trialkylsilyl group; a trialkylstannyl group; a straight-chain or branched, saturated or unsaturated, $C_1$-$C_8$-hydrocarbon, -alkanoyl or alkoxyalkyl radical; an amino group

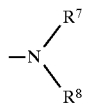

in which $R^7$ and $R^8$, each independently of the other, represents a hydrogen atom or a $C_1$–$C_4$-alkyl group; a corresponding amine oxide

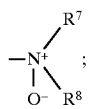

or the grouping —$OR^9$ or —$S(O)_iR^9$ in which i=0, 1 or 2 and $R^9$ represents a hydrogen atom, a methyl, ethyl, propyl, isopropyl, methoxyphenyl, allyl or 2-dimethyl-aminoethyl group; or $R^4$ represents a heteroaromatic radical of formula Iα

 (Iα)

in which A represents a nitrogen, oxygen or sulphur atom, —B—D—E— represents the sequence of elements carbon, carbon, carbon, Nitrogen, carbon, carbon or carbon, nitrogen, carbon and $R^{10}$ represents a hydrogen atom; a cyano group; a chlorine, fluorine, bromine or iodine atom; a trialkylsilyl group; a trialkylstannyl group; a straight-chain or branched, saturated or unsaturated $C_1$–$C_8$-alkyl, -alkanoyl or alkoxyalkyl radical; an
amino group

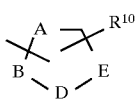

in which $R^7$ and $R^8$, each independently of the other, represents a hydrogen atom or a $C_1C_4$-alkyl group; a corresponding amine oxide

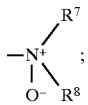

or the grouping —$OR^9$ or —$S(O)_iR^9$ in which i=0, 1 or 2 and $R^9$ represents a hydrogen atom, a methyl, ethyl, propyl, isopropyl, methoxyphenyl, allyl or 2-dimethyl-aminoethyl group;

or $R^4$ represents a heteroaryl radical of formula Iβ

 (Iβ)

in which A represents a nitrogen atom and —B—D—E— represents the sequence of elements —C—C—C—, —N—C—C—, —C—N—C—or —C—C—N—and R10 has the meaning already given, or $R^4$ represents a phenyl radical of formula Iγ

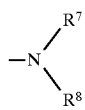 (Iγ)

in which $R^{10}$ has the meaning already given, and

G represents a halogen atom or a $C_1$–$C_4$-alkyl radical when M and Q are hydrogen atoms, or represents a hydrogen atom, a halogen atom or a $C_1$–$C_4$-alkyl radical when M and Q together are an additional bond Q represents a $C_1$–$C_4$-alkyl radical when M and G are hydrogen atoms, wherein when M and Q or M and G are hydrogen atoms, $R^4$ cannot represent an acyl group, or G and M together represent a methylene or ethylene group when Q is a hydrogen atom.

2. A compound according to claim 1, namely

17β-hydroxy-11β-(4-methoxyphenyl)-17α-(prop-1-ynyl)-4,6-oestradien-3-one

17β-hydroxy-11β-(4-methoxyphenyl)-7β-methyl-17α-(prop-1-ynyl)-4-oestren-3-one

17β-hydroxy-11β-(4-methoxyphenyl)-7α-methyl-17α-(prop-1-ynyl)-4-oestren-3-one

11β-[4-(3-acetylphenyl)-phenyl]-17β-hydroxy-17α-(prop-1-ynyl)-4,6-oestradien-3-one 11β-(4-acetylphenyl)-17β-hydroxy-17α-(prop-1-ynyl)-4,6-oestradien-3-one 17β-hydroxy-17α-(3-hydoxyprop-1-(Z)-enyl)-6β-methyl-11β-[4-(3-pyridinyl)-phenyl]-4-oestren-3-one 17β-hydroxy-17α-(3-hydoxyprop-1-(Z)-enyl)-6α-methyl-11β-[4-(3-pyridinyl)-phenyl]-4-oestren-3-one 17β-hydroxy-17α-(3-hydoxyprop-1-ynyl)-6β-methyl-11β-[4-(3-pyridinyl)-phenyl]-4-oestren-3one 6β-bromo-11β-(4-diemthylaminophenyl)-17β-hydroxy-17α-(prop)-1-ynyl)-4-oestren-3-one 6β-bromo-11β-(3-bromo-4-diemthylaminophenyl)-17β-hydroxy-17α-(prop)-1-ynyl)-4oestren-3-one 11β-(4-dimethylaminophenyl)-17β-hydroxy-17α-(prop-1-ynyl)-4,6-oestradien-3-one 11β-(4-dimethylaminophenyl)-17α-ethynyl-17β-hydroxy-4,6-oestradien-3-one 11β-(3-bromo-4-dimethylaminophenyl)-17β-hydroxy-17α-(prop-1-ynyl)-4,6-oestradien-3-one 11β-[4-(4-cyanophenyl)-phenyl]-17β-hydroxy-17α-(prop-1-ynyl)-4,6-oestradien-3-one 11β-[4-(4-cyanophenyl)-phenyl]-17β-hydroxy-17α-(3-hydroxyprop-1-ynyl)-4,6-oestradien-3-one 11β-[4-(4-cyanophenyl)-phenyl]-17β-hydroxy-17α-(3-hydroxyprop-1(Z)-enyl)-4,6-oestradien-3-one 17β-hydroxy-11β-[4-(4-methylthiophenyl)-phenyl]-17α-(prop-1-ynyl)-4,6-oestradien-3-one 17β-hydroxy-17α-(3-hydroxyprop-1-ynyl)-11β-[4-(4-methyl-thiophenyl)-phenyl]-4,6-oestradien-3-one 17β-hydroxy-17α-(3-hydroxyprop-1(Z)-enyl)-11β-[4-(4-methylthiophenyl)-phenyl]-4,6-oestradien-3-one 17β-hydroxy-11β-[4-(4-methylsulphinylphenyl)-phenyl]-17α-(prop-1-ynyl)-4,6-oestradien-3-one 17β-hydroxy-11β-[4-(4-methylsulphonylphenyl)-phenyl]-17α-(prop-1-ynyl)-4,6-oestradien-3-one 11β-[4-(4-acetylphenyl)-phenyl]-17β-hydroxy-17α-(3-hydroxyprop-1(Z)-enyl)-4,6-oestradien-3-one 17β-hydroxy-11β-[4-(3-furanyl)-phenyl]-6β-methyl-17α-(3-hydroxyprop-1(Z)-enyl-4-oestren-3-one 17β-hydroxy-11β-[4-(3-furanyl)-phenyl]-6α-methyl-17α-(3-hydroxyprop-1(Z)-enyl-4-oestren-3-one 11β-[4-(3-furanyl)-phenyl]-17β-hydroxy-17α-(prop-1-ynyl)-4,6-oestradien-3-one 17β-hydroxy-6β-methyl-17α-(3-hydroxyprop-1(Z)-enyl)-11β-[4-(3-thienyl)-phenyl]-4-oestren-3-one 17β-hydroxy-6α-methyl-17α-(3-hydroxyprop-1(Z)-enyl)-11β-[4-(3-thienyl)-phenyl]-4-oestren-3-one 17β-hydroxy-6β-methyl-17α-(3-hydroxyprop-1(Z)-enyl)-11β-[4-(2-thiazolyl)-phenyl]-4-oestren-3-one 17β-hydroxy-6α-methyl-17α-(3-hydroxyprop-1(Z)-enyl)-11β-[4-(2-thiazolyl)-phenyl]-4-oestren-3-one 17β-hydroxy-11β-[4-(5-pyrimidinyl)-phenyl]-6β-methyl-17α-(3-hydroxyprop-1(Z)-enyl)-4-oestren-3-one 17β-hydroxy-11β-[4-(5-pyrimidinyl)-phenyl]-6α-methyl-17α-(3-hydroxyprop-1(Z)-enyl)-4-oestren-3-one 17β-hydroxy-11β-[4-(5-pyrimidinyl)-phenyl]-6β-methyl-17α-(prop-1-ynyl)-4-oestren-3-one 17β-hydroxy-17α-(prop-1-ynyl)-11β-[4-(5-pyrimidinyl)-phenyl]-4,6-oestradien-3-one 17α-cyanomethyl-17β-hydroxy-11β-(4-hydroxyphenyl)-4,6-oestradien-3-one 11β-(4-acetylphenyl)-17α-cyanomethyl-17β-hydroxy-4,6-oestradien-3-one 17α-cyanomethyl-17β-hydroxy-11β-[4-(2-propenyl)-phenyl]-4,6-oestradien-3-one 17α-cyanomethyl-17β-hydroxy-11β-[4-(4-methylthiophenyl)-phenyl]-4,6-oestradien-3-one.

3. Pharmaceutical compositions that comprise at least one compound according to claim 1 as well as a pharmeceutical carrier.

4. A method of using compounds according to claim 1 for the preparation af medicaments which comprises combining one or more compounds of formula I.

\* \* \* \* \*

UNITED STATES PATENT AND TRADEMARK OFFICE
CERTIFICATE OF CORRECTION

PATENT NO.  : 5,843,931
DATED       : December 1, 1998
INVENTOR(S) : Eckhard Ottow et al.

It is certified that error appears in the above-identified patent and that said Letters Patent is hereby corrected as shown below:

On the title page:

Item: (73) on the first page of the patent, "Shering" should read --Schering--.

Signed and Sealed this

Ninth Day of November, 1999

*Attest:*

Q. TODD DICKINSON

*Attesting Officer*     *Acting Commissioner of Patents and Trademarks*